US010610489B2

(12) United States Patent
Schneider et al.

(10) Patent No.: US 10,610,489 B2
(45) Date of Patent: Apr. 7, 2020

(54) PHARMACEUTICAL COMPOSITION, PHARMACEUTICAL DOSAGE FORM, PROCESS FOR THEIR PREPARATION, METHODS FOR TREATING AND USES THEREOF

(75) Inventors: Peter Schneider, Ulm (DE); Wolfram Eisenreich, Ulm (DE); Nantharat Pearnchob, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/894,385

(22) Filed: Sep. 30, 2010

(65) Prior Publication Data
US 2011/0236477 A1    Sep. 29, 2011

(30) Foreign Application Priority Data
Oct. 2, 2009   (EP) ..................................... 09172081

(51) Int. Cl.
| *A61K 9/20* | (2006.01) |
| *A61K 9/28* | (2006.01) |
| *A61K 31/155* | (2006.01) |
| *A61K 45/06* | (2006.01) |
| *A61K 9/24* | (2006.01) |
| *A61K 31/351* | (2006.01) |

(52) U.S. Cl.
CPC .......... *A61K 9/2072* (2013.01); *A61K 9/2009* (2013.01); *A61K 9/209* (2013.01); *A61K 9/2018* (2013.01); *A61K 9/2027* (2013.01); *A61K 9/2054* (2013.01); *A61K 9/2059* (2013.01); *A61K 9/2866* (2013.01); *A61K 31/155* (2013.01); *A61K 31/351* (2013.01); *A61K 45/06* (2013.01)

(58) Field of Classification Search
None
See application file for complete search history.

(56) References Cited

U.S. PATENT DOCUMENTS

| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,145,684 A | 9/1992 | Liversidge et al. |
| 5,807,580 A | 9/1998 | Luber |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,294,618 B2 | 11/2007 | Fushimi et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 * | 12/2010 | Bindra et al. ................. 514/460 |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |

(Continued)

FOREIGN PATENT DOCUMENTS

| CA | 2382480 A1 | 3/2001 |
| CA | 2388818 A1 | 4/2001 |

(Continued)

OTHER PUBLICATIONS

Drug Watch—"Type 2 diabetes mellitus" Formulary vol. 43 Aug. 2008.*

(Continued)

*Primary Examiner* — Susan T Tran

(74) *Attorney, Agent, or Firm* — Edouard G. Lebel

(57) ABSTRACT

The present invention relates to pharmaceutical compositions comprising fixed dose combinations of a SGLT-2 inhibitor drug and a partner drug, processes for the preparation thereof, and their use to treat certain diseases.

29 Claims, No Drawings

(56) References Cited

U.S. PATENT DOCUMENTS

| | | |
|---|---|---|
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 9,024,010 B2 | 5/2015 | Weber et al. |
| 9,127,034 B2 | 9/2015 | Eckhardt et al. |
| 9,192,616 B2 | 11/2015 | Johnson |
| 9,192,617 B2 | 11/2015 | Mayoux et al. |
| 9,949,997 B2 | 4/2018 | Broedl et al. |
| 9,949,998 B2 | 4/2018 | Broedl et al. |
| 10,258,637 B2 | 4/2019 | Broedl et al. |
| 10,406,172 B2 | 9/2019 | Eickelmann et al. |
| 2001/0041674 A1 | 11/2001 | Tomiyama et al. |
| 2001/0044435 A1 | 11/2001 | Himmelsbach et al. |
| 2002/0137903 A1 | 9/2002 | Ellsworth et al. |
| 2002/0173509 A1 | 11/2002 | Himmelsbach et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0097510 A1 | 5/2004 | Himmelsbach et al. |
| 2004/0138148 A1 | 7/2004 | Fushimi et al. |
| 2004/0138439 A1 | 7/2004 | Deshpande et al. |
| 2004/0247677 A1* | 12/2004 | Oury ............... A61K 9/209 424/472 |
| 2004/0259819 A1 | 12/2004 | Frick et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0187168 A1 | 8/2005 | Eickelmann et al. |
| 2005/0209166 A1* | 9/2005 | Eckhardt et al. ............ 514/23 |
| 2005/0233982 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0210627 A1 | 9/2006 | Pfeffer et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0042042 A1* | 2/2007 | Jo ............... A61K 9/0065 424/468 |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0107731 A1 | 5/2008 | Kohlrausch et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0137499 A1 | 5/2009 | Honda et al. |
| 2009/0281078 A1 | 11/2009 | Routledge et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0077212 A1 | 3/2011 | Seed et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0041069 A1 | 2/2012 | Sesha |
| 2012/0071403 A1* | 3/2012 | Strumph et al. ............... 514/5.3 |
| 2012/0094894 A1 | 4/2012 | Graefe-Mody et al. |
| 2012/0196812 A1 | 8/2012 | Eickelmann et al. |
| 2012/0219622 A1 | 8/2012 | Kohlrausch et al. |
| 2012/0283169 A1 | 11/2012 | Grempler et al. |
| 2012/0296080 A1 | 11/2012 | Eckhardt et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2015/0322053 A1 | 11/2015 | Eckhardt et al. |
| 2016/0000816 A1 | 1/2016 | Broedl et al. |
| 2016/0030385 A1 | 2/2016 | Manuchehri et al. |
| 2016/0038523 A1 | 2/2016 | Broedl et al. |
| 2016/0038524 A1 | 2/2016 | Broedl et al. |
| 2016/0038525 A1 | 2/2016 | Broedl et al. |
| 2016/0074415 A1 | 3/2016 | Wienrich et al. |
| 2017/0020907 A1 | 1/2017 | Eickelmann et al. |
| 2017/0095424 A1 | 4/2017 | Ito et al. |
| 2017/0106009 A1 | 4/2017 | Mayoux |
| 2017/0189437 A1 | 7/2017 | Manuchehri et al. |
| 2017/0266152 A1 | 9/2017 | Broedl et al. |
| 2017/0305952 A1 | 10/2017 | Klein et al. |
| 2017/0333465 A1 | 11/2017 | Broedl et al. |
| 2018/0104249 A1 | 4/2018 | Eisenreich |
| 2018/0104268 A1 | 4/2018 | Mayoux et al. |
| 2018/0125813 A1 | 5/2018 | von Eynatten et al. |
| 2018/0169126 A1 | 6/2018 | Broedl et al. |
| 2018/0177794 A1 | 6/2018 | Wienrich et al. |
| 2018/0185291 A1 | 7/2018 | Ito et al. |
| 2018/0193427 A1 | 7/2018 | Grempler et al. |
| 2018/0200278 A1 | 7/2018 | Broedl et al. |
| 2018/0214468 A1 | 8/2018 | Broedl et al. |
| 2018/0289678 A1 | 10/2018 | Eisenreich et al. |
| 2018/0318251 A1 | 11/2018 | Broedl et al. |
| 2018/0344647 A1 | 12/2018 | Boeck et al. |
| 2019/0015437 A1 | 1/2019 | Broedl et al. |
| 2019/0038654 A1 | 2/2019 | Broedl et al. |
| 2019/0134072 A1 | 5/2019 | Broedl et al. |
| 2019/0209596 A1 | 7/2019 | Mayoux |
| 2019/0298749 A1 | 10/2019 | Mayoux et al. |
| 2019/0309004 A1 | 10/2019 | Wirth et al. |
| 2019/0350894 A1 | 11/2019 | Broedl et al. |
| 2019/0350957 A1 | 11/2019 | Broedl et al. |

FOREIGN PATENT DOCUMENTS

| | | |
|---|---|---|
| CA | 2437240 A1 | 8/2002 |
| CA | 2494177 A1 | 2/2004 |
| CA | 2496249 A1 | 3/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2548353 A1 | 7/2005 |

(56) References Cited

FOREIGN PATENT DOCUMENTS

| | | |
|---|---|---|
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2649922 A1 | 11/2007 |
| CA | 2651019 A1 | 11/2007 |
| CA | 2720450 A1 | 10/2009 |
| CN | 101503399 A | 8/2009 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1852108 A1 | 11/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2002338471 A | 11/2002 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| JP | 2008540373 A | 11/2008 |
| WO | 9831697 A1 | 7/1998 |
| WO | 0116147 A1 | 3/2001 |
| WO | 0127128 A1 | 4/2001 |
| WO | 0174834 A1 | 10/2001 |
| WO | 02064606 A1 | 8/2002 |
| WO | 2002083066 A2 | 10/2002 |
| WO | 2003020737 A1 | 3/2003 |
| WO | 2003031458 A1 | 4/2003 |
| WO | 2003078404 A1 | 9/2003 |
| WO | 2003099836 A1 | 12/2003 |
| WO | 2004007517 A1 | 1/2004 |
| WO | 2004013118 A1 | 2/2004 |
| WO | 2004018468 A2 | 3/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 9/2004 |
| WO | 2005011786 A1 | 2/2005 |
| WO | 2005012318 A2 | 2/2005 |
| WO | 2005012326 A1 | 2/2005 |
| WO | 2005021566 A2 | 3/2005 |
| WO | 2005049022 A2 | 6/2005 |
| WO | 2005063785 A2 | 7/2005 |
| WO | 2005067976 A2 | 7/2005 |
| WO | 2005085237 A1 | 9/2005 |
| WO | 2005085265 A1 | 9/2005 |
| WO | 2005092877 A1 | 10/2005 |
| WO | 2005117861 A1 | 12/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006064033 A2 | 6/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007136116 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008131149 A2 | 10/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2010045656 A1 | 4/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012106303 A1 | 8/2012 |
| WO | 2012107476 A1 | 8/2012 |
| WO | 2012120040 A1 | 9/2012 |
| WO | 2013007557 A1 | 1/2013 |
| WO | 2013106547 A1 | 7/2013 |
| WO | 2013131967 A1 | 9/2013 |
| WO | 2013139777 A1 | 9/2013 |

OTHER PUBLICATIONS

Jones, Byrony "Empagliflozin—one step closer to glycaemic control in patients with type II diabetes and CKD?" (2014) Nature Reviews Nephrology 10, 181, 2 pgs.

Kadowaki, T et al. "PPAR gamma agonist and antagonist" Nihon Yakurigaku Zasshi (2001) vol. 118, No. 9, pp. 321-326. (English abstract).

Knochel, Paul et al. "Highly functionalized Organomagnesium Reagents Prepared through Halogen-Metal Exchange" Angew. Chem. INt. Ed. (2003) vol. 42, 4302-4320.

(56) References Cited

OTHER PUBLICATIONS

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Krasovskiy Arkady et al. "A LiCL-Mediated Br/Mg Exchange Reaction for the Preparation of Functionalized Aryl- and Heterarylmagnesium Compounds from Organic Bromides**" Angew. Chem. Int. Ed. (2004) vol. 43, pp. 3333-3336.

Kuribayashi, Takeshi., et al; Bis C-Glycosylated Diphenylmethanes for Stable Glycoepitope Mimetics; Syntletters (1999) vol. 6 pp. 737-740.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.

Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.

Lieberman, Joseph A. "Metabolic Changes Associated with Antipsychotic Use" Prim Care Companion J Clinc Psychiatry (2004) 6, pp. 8-13.

Lipworth, Brian J. "Clinical pharmacology of b3-adrenoceptors" Br J Clin Pharmacol (1996) pp. 291-300.

Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.

Magee, G.M. et al. "Is hyperfiltration associated with the future risk of developing diabetic nephropathy? A meta-analysis" Diabetologia (2009) 52: pp. 691-697.

Malatiali, Slava et al. "Phlorizin Prevents Glomerular Hyperfiltration but not Hypertrophy in Diabetic Rats" (2008) Experimental Diabetes Research, vol. 2008, 7 pgs.

McHale, Mary "Grignard Reaction" Connexions module: m15245, (2007) pp. 1-18.

McLaughlin, Mark., et al; Suzuki-Miyaura Cross-Coupling of Benzylic Phospahates with Arylboronic Acids; Organic Letters (2005) vol. 7 No. 22 pp. 4875-4878.

McMaster University, Chem2006 Lab Manual, 1997/98, Expt 1, Part B, pp. 1-9.

Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.

Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.

Miller, Del D. "Review and Management of Clozapine Side Effects" (2000) J Clinc Psychiatry, 61 (Suppl 8) pp. 14-17.

Mooradian, Arsharg D. et al. "Narrative Review: A Rational Approach to Starting Insulin Therapy" (2006) Annals of Internal Medicine, vol. 145, pp. 125-134.

Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Oku, Akira., et al; T-1095, An Inhibitor or renal Na+-Glucose Cotransporters, May Provide a Novel Approach to Treating Diabetes; Diabetes (1999) vol. 48 pp. 1794-1800.

Panchapakesan, Usha et al. Effects of SGLT2 Inhibition in Human Kidney Proximal Tubular Cells—Renoprotection in Diabetic Nephropathy? PLoS one, (2013) vol. 8, Issue 2, e54442, 8 pgs.

Patil, Basanagouda M. et al. "Elevation of systolic blood pressure in an animal model of olanzapine induced weight gain" (2006) European Journal of Pharmacology, vol. 551, pp. 112-115.

Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Piya, Milan K. et al. "Emerging treatment options for type 2 diabetes" British Journal of Clinical Pharmacology, (2010) vol. 70, No. 5, pp. 631-644.

Powers, Richard E. et al. "Understanding the Side Effects of Neuroleptics" (2008) Bureau of Geriatric Psychiatry/DETA, pp. 17-24.

Printz, Richard L. et al. "Tweaking the Glucose Sensor: Adjusting Glucokinase Activity with Activator Compounds" Endocrinology, (2005) vol. 146, No. 9, pp. 3693-3695.

Rainier, Jon D. et al. "Aluminum- and Boron-Mediated C-Glycoside Synthesis from 1,2-Anhydroglycosides" Organic Letters, (2000) vol. 2, No. 17, pp. 2707-2709.

Randzio, Stanislaw L. et al. "Metastability and Instability of Organic Crystalline Substances" J. Phys. Chem. (2008) 112, pp. 1435-1444.

Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.

Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Rieusset, Jennifer et al. "Insulin Acutely Regulates the Expression of the Peroxisome Proliferator-Activated Receptor-y in Human Adipocytes" (1999) Diabetes, vol. 48, pp. 699-705.

Ritchie, C.W. et al. "The impact upon extra-pyramidal side effects, clinical symptoms and quality of life of a switch from conventional to atypical antipsychotics (risperidone or olanzapine) in elderly patients with schizophrenia" (2003) International Journal of Geriatric Psychiatry, vol. 18, pp. 432-440.

Rudnic, Edward et al. "Oral Solid Dosage Forms" Remington's Pharmaceutical Sciences, 18th Ed, Gennaro, A.R. Ed, Macie Pub. Co. (1990) pp. 1633-1665.

Sherwin, Robert S. et al. "The Prevention or Delay of Type 2 Diabetes" Diabetes Care, (2002) vol. 25, No. 4, pp. 742-749.

Silverman, et al. "Handbook of Grignard Reagents" Marcel Dekker (1996) p. 82.

Singhal, Dharmendra et al. "Drug polymorphism and dosage form design: a practical perspective" Advanced Drug Delivery Reviews, 56, (2004) pp. 335-347.

Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Stella, Valentino J. "Prodrugs as therapeutics" (2004) Ashley Publications, vol. 14, No. 3, pp. 277-280.

Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) LIver International, vol. 31, 9, pp. 1285-1297.

Tanaka, Chikako "Therapeutic Drugs for Metabolic Diseases, Chapter 2" (2002) New Yakurigaku (New Pharmacology) pp. 524-527.

(56) References Cited

OTHER PUBLICATIONS

Testa, Bernard "Prodrug research: futile or fertile?" (2004) Biochemical Pharmacology vol. 68, pp. 2097-2106.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.
Threlfall, Terry "Structural and Thermodynamic Explanations of Ostwald's Rule" Organic Process Research & Development (2003) vol. 7, pp. 1017-1027.
Tsujihara, Kenji et al. "Na+-Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.
Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.
U.S. Appl. No. 14/253,935, filed Apr. 16, 2014. Inventor: Uli Christian Broedl.
Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.
Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.
Vervoort, G. et al. "Glomerular hyperfiltration in type 1 diabetes mellitus results from primary changes in proximal tubular sodium handling without changes in volume expansion" (2005) European Journal of Clinical Investigation vol. 35, pp. 330-336.
Wallace, Debra J., et al; Cyclopropylboronic Acid: Synthesis and Suzuki Cross-Coupling Reactions; Tetrahedron Letters (2002) vol. 43 pp. 6987-6990; Pergamon Press.
Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.
Websters Third New International Dictionary, Editor: GOVE, definition of prevent; 1963, 2 pgs.
Wolff, Manfred E., et al., "Burger's Medicinal Chemistry and Drug Discovery, Fifth Edition, vol. 1, Principles and Practices", (1994) Wiley-Interscience Publication pp. 975-976.
Woo, Young Sup et al. "Blood pressure changes during clozapine or olanzapine treatment in Korean schizophrenic patients" (2009) The World Journal of Biological Psychiatry, vol. 10(4); pp. 420-425.
Wu, Ren-Rong et al. "Lifestyle Intervention and Metformin for Treatment of Antipsychotic-Induced Weight Gain, A Randomized Controlled Trial" Journal of American Medical Association (2008) V 299, pp. 185-193.
Xue, Song., et al; Zinc-mediated Synthesis of Alpha-C-Glycosided from 1,2-Anhydroglycosides; Synletters (2003) vol. 6 pp. 870-872.
Yamada, Yuichiro et al. "Clinic: Careful Progress in the Field and new Therapeutic Methods" Medical Online, (2007) vol. 220, No. 13, pp. 1219-1221.
Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. vol. 54, pp. 166-178.
Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.
Abstract ASN09L1_307a "Contact View (TH-P0751) Kidney Function and Response to Diabetes in Mice Lacking SGLT2", Vallon, Volker et al, Oct. 29, 2009, 1 pg.
Abstract ASN09L1_4153a, "Contact View (SA-P02723) Chronic SGLT2 Blockade Reduces Proximal Reabsorption and Normalizes State of Tubuloglomerular Feedback Activation in Hyperfiltering Diabetic Rats" Thomson, Scott et al., Oct. 31, 2009, 1 pg.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
American Diabetes Association "Consensus Development Conference on Antipyschotic Drugs and Obesity and Diabetes" (2004) Diabetes Care, vol. 27, No. 2, pp. 596-601.
American Diabetes Association "Diagnosis and Classification of Diabetes Mellitus" Diabetes Care, vol. 33, Supplement 1, Jan. 2010. pp. S62-S69.
Anonymous "Efficacy and Safety of Empagliflozin (BI 10773) in Patients with Type 2 Diabetes and Renal Impairment" Jan. 8, 2013, XP055120166, www.clinicaltrials.gov/ct2/show/study/NCT01164501?term=empagliflozin&rank=26.
Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.
Ault Addison, "Techniques and experiments for organic chemistry" University Science Books, 1998, pp. 59-60.
Baptista, Trino et al. "Pharmacological Management of Atypical Antipsychotic-Induced Weight Gain" (2008) CNS Drugs, 22, 6, pp. 478-495.
Barnett, Anthony H. et al. "Efficacy and safety of empagliflozin added to existing antidiabetes treatments in patients with type 2 diabetes and chronic kidney disease: a randomised, double-blind, placebo-controlled trial" The Lancet, (2014) vol. 2, pp. 369-384.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Bloomgarden, Zachary T. "Diabetes Treatment" Diabetes Care, (Mar. 2009) vol. 32, No. 3 pp. e25-e30.
Boyda, Heidi N et al. "Preclinical models of antipsychotic drug-induced metabolic side effects" (2010) Trends in Pharmacological Sciences vol. 31, pp. 484-497.
Byrn, Stephen et al. "Pharmaceutical Solids: A Strategic Approach to Regulatory Considerations" Pharmaceutical Research, vol. 12, No. 7, (1995) pp. 945-954.
Castelhano, Arlindo L. et al. "Reactions of an Electrophilic Glycine Cation Equivalent With Grignard Reagents a Simple Synthesis of β,g-Unsaturated Amino Acids" (1986) Tetrahedron Letters, vol. 27, No. 22, pp. 2435-2438.
Cernea Simona. et al. "β-Cell Protection and Therapy for Latent Autoimmune Diabetes in Adults" Diabetes Care (2009) vol. 32, Supplement 2, pp. S246-S252.
Deacon, Carolyn F. "Perspectives in Diabetes Therapeutic Strategies Based on Glucagon-Like Peptide 1" Diabetes, (2004) vol. 53 pp. 2181-2189.
Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.
Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.
Drug Watch "Type 2 Diabetes Mellitus" Formulary vol. 43 Aug. 2008 p. 304.
Ellinger, Lara K. et al. "Efficacy of Metformin and Topiramate in Prevention and Treatment of Second-Generation Antipsychotic-Induced Weight Gain" Annals of Pharmacotherapy (2010) vol. 44, No. 4, pp. 668-679.

(56) References Cited

OTHER PUBLICATIONS

EMBASE Database. Accession No. 0050872772. Jelsing, J et al. "Empagliflozin a novel sodium glucose cotransporter-2 inhibitor improves glucose homeostasis and preserves pancreatic beta cell mass in db/db mice" (2012) 2 pgs.

EMBASE database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.

Ettmayer, Peter et al. "Lessons Learned from Marketed and Investigational Prodrugs" (2004) Journal of Medicinal Chemistry, vol. 47, No. 10, pp. 2393-2404.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.

Ghassemi et al. "Synthesis and properties of new sulfonated poly(p-phenylene) derivatives for proton exchange membranes" Polymer (2004) pp. 5847-5854.

Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.

Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.

Greco, Gary T. et al. "Segregation of Active Constituents from Tablet Formulations During Grinding: Theoretical Considerations" Drug Development and Industrial Pharmacy, (1982) 8(4), pp. 565-578.

Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.

Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Henderson, David C. et al. "Clozapine and Hypertension: A Chart Review of 82 Patients" (2004) J Clin Psychiatry, 65, pp. 686-689.

Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

International Search Report for PCT/EP2005/002618 dated Jun. 30, 2005.

International Search Report for PCT/EP2005/056806 dated Dec. 27, 2006.

International Search Report for PCT/EP2006/061956 dated Jul. 5, 2006.

International Search report for PCT/EP2006/061957 dated Jul. 5, 2006.

International Search Report for PCT/EP2007/062023 dated Sep. 17, 2008.

International Search Report for PCT/EP2010/051735 dated May 20, 2010.

International Search Report for PCT/EP2010/051736 dated May 7, 2010.

International Search Report for PCT/EP2010/051737 dated May 7, 2010.

International Search Report for PCT/EP2010/064619 dated Jan. 20, 2011.

International Search Report for PCT/EP2012/053910 dated May 14, 2012.

International Search Report for PCT/EP2013/054524 dated May 6, 2013.

Isaji, Masayuki "Sodium-glucose cotransporter inhibitors for diabetes" Current Opinion in Investigational Drugs, (2007) vol. 8, No. 4, pp. 285-292.

Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.

Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

Buhler, Volker "Kollidon® Polyvinylpyrrolidone excipients for the pharmaceutical industry" 9th revised edition, Mar. 2008, 1-331.

Joshi, Shashank R. "Metformin: Old Wine in New Bottle—Evolving Technology and Therapy in Diabetes" Journal of Association of Physicians in India, (2005) vol. 53, pp. 963-972.

Anonymous, "Composition with a High Drug Load of Empagliflozin" Feb. 26, 2016, 3 pgs.

Aulton, Michael E. "Pharmaceutics, The Science of Dosage Form Design" (2002) 2nd Edition, 404-409.

Bauer, Kurt H. et al. "Pharmazeutische Technologie" (1993) p. 293.

Colorcon; Opadry II Aqueous Film Coating; http://www.colorcon.com/products-formulation/all-products/film-coatings/immediate-release/opadry-II; Dec. 31, 2015.

Fiese, Eugene F et al. "Preformulation" (1987) The Theory and Practice of Industrial Pharmacy, 28 pgs.

Gennaro, Alfonso R. "Remington: The Science and Practice of Pharmacy" Twentieth Edition (2000) 4 pgs.

Lieberman, Herbert A. et al. "Pharmaceutical Dosage Forms: Tablets, vol. 1" (1989) pp. 5-6.

Swarbrick et al., Encyclopedia of Pharmaceutical Technology, 2nd Edition, (2002) 4 pgs.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, 556-563.

Baati, Rachid et al. "A Convenient Synthesis of 2-Tetrahydrofuranyl Ethers" (2000) Organic Letters, vol. 2, No. 4, 485-487.

Brazg, R et al. "Effect of Adding MK-0431 to Ongoing Metformin Therapy in Type 2" (2005) Diabetes, vol. 54, Suppl. 1, A3.

Caira, Mino R. "Crystalline Polymorphism of Organic Compounds" (1998) Topics in Current Chemistry, vol. 198, 164-208.

Gong, Hegui et al. "A Room Temperature Negishi Cross-Coupling Approach to C-Alkyl Glycosides" (2007) Journal of the American Chemical Society, vol. 129, 1908-1909.

Guillory, J. Keith "Generation of Polymorphs, Hydrates, Solvates and Amorphous Solids" Polymorphism in Pharmaceutical Solids (1999) 46 pgs.

Hu, Gongzheng. "Zoopharmacy" China Agriculture Press, Section 4, (2008) pp. 32-33.

McKinney, James D. et al. "The Practice of Structure Activity Relationships (SAR) in Toxicology" (2000) Toxicological Sciences, vol. 56, 8-17.

Negishi, Ei-ichi, et al. "Selective Carbon-Carbon Bond Formation via Transition Metal Catalysis. 3. A Highly Selective Synthesis of Unsymmetrical Biaryls and Diarylmethanes by the Nickel- or

(56) References Cited

OTHER PUBLICATIONS

Palladium-Catalyzed Reaction of Aryl- and Benzylzinc Derivatives with Aryl Halides" (1977) Journal of Organic Chemistry, V 42, No. 10, 1821-1823.

Robinson, J.A. "Chemical and Biochemical Aspects of Polyether-Ionophore Antibiotic Biosynthesis" (1991) Progress in the Chemistry of Organic Natural Products, 1-81.

Sturtevant Inc. "Micronizer Jet Mill" (2000), 6 pgs.

Yuan, Yingjin. "Modern Pharmaceutical Technology", Chemical Industry Press, (2005) vol. 2, p. 75.

Cherney, David Z.I. et al. "The effect of empagliflozin on arterial stiffness and heart rate variability in subjects with uncomplicated type 1 diabetes mellitus" (2014) Cardiovascular Diabetology, 13:28, 8 pgs.

Insalaco, Monica et al. "Sodium Glucose Co-transporter Type 2 (SGLT2) Inhibitors in CKD" (2015) Nefrologia, vol. 32, No. 4, pp. 1-9.

Mende, Christian "Management of Chronic Kidney Disease: The Relationship between Serum Uric Acid and the Development of Nephropathy" (2015) Adv. Ther. 32, 1177-1191.

Zanoli, L. et al . "Sodium-Glucose Linked Transporter-2 Inhibitors in Chronic Kidney Disease" (2015) The Scientific World Journal, Article ID 317507, 6 pgs.

Rosenstock, Julio et al. "Dual Add-on Therapy in Type 2 Diabetes Poorly Controlled with Metformin Monotherapy: A Randomized Double-Blind Trial of Saxagliptin Plus Dapagliflozin Addition Versus Single Additon of Saxagliptin or Dapagliflozin to Metformin" (2015) Diabetes Care, vol. 38: 376-383.

Clinical Trials: NCT01811953 "History of Changes for Study: NCT01811953, Equivalence of Resorption of Empagliflozin/Metformin Administered as Combination Tablet Compared With Empagliflozin/Metformin as Single Tablets Administered Together" Sponsor: Boehringer Ingelheim, Lastest version Jun. 26, 2015, 6 pgs.

Woerle Hans-Juergen et al. "Safety and Efficacy of Empagliflozin as Monotherapy or Add-on to Metformin in a 78-Week Open-Lable Extension Study in Patients with Type 2 Diabetes" Presentation Abstract, 49-LB, (2012) 4 pg.

\* cited by examiner

PHARMACEUTICAL COMPOSITION, PHARMACEUTICAL DOSAGE FORM, PROCESS FOR THEIR PREPARATION, METHODS FOR TREATING AND USES THEREOF

TECHNICAL FIELD OF THE INVENTION

The present invention relates to pharmaceutical compositions comprising fixed dose combinations of a SGLT-2 inhibitor drug and a partner drug, processes for the preparation thereof, and their use to treat certain diseases.

In a more detailed aspect, the present invention relates to oral solid dosage forms for fixed dose combination (FDC) of a selected SGLT-2 inhibitor drug and a certain partner drug. In addition the invention relates to a process for the preparation of such a pharmaceutical dosage form. In addition the invention relates to the use of the pharmaceutical composition and of the pharmaceutical dosage form in the treatment and/or prevention of selected diseases and medical conditions, in particular of one or more conditions selected from type 1 diabetes mellitus, type 2 diabetes mellitus, impaired glucose tolerance, impaired fasting blood glucose and hyperglycemia inter alia. Furthermore the present invention relates to methods of treating and/or preventing of such diseases and medical conditions wherein a pharmaceutical composition or pharmaceutical dosage form according to the invention is administered to a patient in need thereof.

BACKGROUND OF THE INVENTION

Type 2 diabetes is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes is associated with a two to five fold increase in cardiovascular disease risk.

After long duration of disease, most patients with type 2 diabetes will eventually fail on oral therapy and become insulin dependent with the necessity for daily injections and multiple daily glucose measurements.

The UKPDS (United Kingdom Prospective Diabetes Study) demonstrated that intensive treatment with metformin, sulfonylureas or insulin resulted in only a limited improvement of glycemic control (difference in HbA1c ~0.9%). In addition, even in patients within the intensive treatment arm glycemic control deteriorated significantly over time and this was attributed to deterioration of β-cell function. Importantly, intensive treatment was not associated with a significant reduction in macrovascular complications, i.e. cardiovascular events. Therefore many patients with type 2 diabetes remain inadequately treated, partly because of limitations in long term efficacy, tolerability and dosing inconvenience of existing antihyperglycemic therapies.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

The high incidence of therapeutic failure is a major contributor to the high rate of long-term hyperglycemia-associated complications or chronic damages (including micro- and macrovascular complications such as e.g. diabetic nephropathy, retinopathy or neuropathy, or cardiovascular complications) in patients with type 2 diabetes.

Therefore, there is an unmet medical need for methods, medicaments and pharmaceutical compositions with a good efficacy with regard to glycemic control, with regard to disease-modifying properties and with regard to reduction of cardiovascular morbidity and mortality while at the same time showing an improved safety profile.

SGLT2 inhibitors inhibitors represent a novel class of agents that are being developed for the treatment or improvement in glycemic control in patients with type 2 diabetes. Glucopyranosyl-substituted benzene derivative are described in the prior art as SGLT2 inhibitors, for example in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940. The glucopyranosyl-substituted benzene derivatives are proposed as inducers of urinary sugar excretion and as medicaments in the treatment of diabetes.

Renal filtration and reuptake of glucose contributes, among other mechanisms, to the steady state plasma glucose concentration and can therefore serve as an antidiabetic target. Reuptake of filtered glucose across epithelial cells of the kidney proceeds via sodium-dependent glucose cotransporters (SGLTs) located in the brush-border membranes in the tubuli along the sodium gradient. There are at least 3 SGLT isoforms that differ in their expression pattern as well as in their physico-chemical properties. SGLT2 is exclusively expressed in the kidney, whereas SGLT1 is expressed additionally in other tissues like intestine, colon, skeletal and cardiac muscle. SGLT3 has been found to be a glucose sensor in interstitial cells of the intestine without any transport function. Potentially, other related, but not yet characterized genes, may contribute further to renal glucose reuptake. Under normoglycemia, glucose is completely reabsorbed by SGLTs in the kidney, whereas the reuptake capacity of the kidney is saturated at glucose concentrations higher than 10 mM, resulting in glucosuria ("diabetes mellitus"). This threshold concentration can be decreased by SGLT2-inhibition. It has been shown in experiments with the SGLT inhibitor phlorizin that SGLT-inhibition will partially inhibit the reuptake of glucose from the glomerular filtrate into the blood leading to a decrease in blood glucose concentrations and to glucosuria.

AIM OF THE PRESENT INVENTION

The aim of the present invention is to provide a pharmaceutical composition comprising a SGLT2 inhibitor and a partner drug which has high content uniformity for the SGLT2 inhibitor and the partner drug.

Another aim of the present invention is to provide a pharmaceutical composition comprising a SGLT2 inhibitor and a partner drug which has very high drug load for the partner drug and very low drug load for the SGLT2 inhibitor.

Another aim of the invention is to provide a pharmaceutical composition comprising a SGLT2 inhibitor and a partner drug which allows an effective production with regard to time and costs of pharmaceutical dosage forms.

Another aim of the present invention is to provide a pharmaceutical composition comprising a SGLT-2 inhibitor and a partner drug which avoids or reduces sticking and capping during the production process of the composition.

Another aim of the present invention is to provide a pharmaceutical composition comprising a SGLT-2 inhibitor and a partner drug which avoids or reduce filming during the production process of the composition.

Another aim of the present invention is to provide a pharmaceutical dosage form comprising a SGLT-2 inhibitor and a partner drug which has an acceptable size.

Another aim of the invention is to provide a pharmaceutical dosage form comprising a SGLT-2 inhibitor and a partner drug which has a short disintegration time, which has good dissolution properties and/or which enables a high bioavailability of the SGLT-2 inhibitor in a patient.

Another aim of the invention it to provide a pharmaceutical composition and a pharmaceutical dosage form, each comprising a SGLT2 inhibitor and a partner drug, and a method for preventing, slowing progression of, delaying or treating a metabolic disorder, in particular of type 2 diabetes mellitus.

A further aim of the present invention is to provide a pharmaceutical composition and a pharmaceutical dosage form, each comprising a SGLT2 inhibitor and a partner drug, and a method for improving glycemic control in a patient in need thereof, in particular in patients with type 2 diabetes mellitus.

Another aim of the present invention is to provide a pharmaceutical composition and a pharmaceutical dosage form, each comprising a SGLT2 inhibitor and a partner drug, and a method for improving glycemic control in a patient with insufficient glycemic control.

Another aim of the present invention is to provide a pharmaceutical composition and a pharmaceutical dosage form, each comprising a SGLT2 inhibitor and a partner drug, and a method for preventing, slowing or delaying progression from impaired glucose tolerance (IGT), impaired fasting blood glucose (IFG), insulin resistance and/or metabolic syndrome to type 2 diabetes mellitus.

Yet another aim of the present invention is to provide a pharmaceutical composition and a pharmaceutical dosage form, each comprising a SGLT2 inhibitor and a partner drug, and a method for preventing, slowing progression of, delaying or treating of a condition or disorder from the group consisting of complications of diabetes mellitus.

A further aim of the present invention is to provide a pharmaceutical composition and a pharmaceutical dosage form, each comprising a SGLT2 inhibitor and a partner drug, and a method for reducing the weight or preventing an increase of the weight in a patient in need thereof.

Another aim of the present invention is to provide a pharmaceutical composition and a pharmaceutical dosage form, each comprising a SGLT2 inhibitor and a partner drug, with a high efficacy for the treatment of metabolic disorders, in particular of diabetes mellitus, impaired glucose tolerance (IGT), impaired fasting blood glucose (IFG), and/or hyperglycemia, which has good to very good pharmacological and/or pharmacokinetic and/or physicochemical properties.

Another aim of the present invention is to provide a process for the preparation of a pharmaceutical dosage form according to the invention which is effective in costs and/or time.

Further aims of the present invention become apparent to the one skilled in the art by description hereinbefore and in the following and by the examples.

SUMMARY OF THE INVENTION

In one aspect the present invention provides a pharmaceutical composition comprising a SGLT-2 inhibitor and a partner drug as a active pharmaceutical ingredients and one or more excipients. In one aspect, a pharmaceutical composition according to the invention is a solid pharmaceutical composition, for example a solid pharmaceutical composition for oral administration.

In one aspect, partner drugs to be combined with the SGLT-2 inhibitor within the pharmaceutical compositions according to this invention are biguanides (e.g. metformin such as metformin hydrochloride).

A preferred partner drug within the meaning of this invention is metformin, particularly metformin hydrochloride (1,1-dimethylbiguanide hydrochloride or metformin HCl).

In general, pharmaceutical excipients which may be used may be selected from the group consisting of one or more fillers, one or more binders or diluents, one or more lubricants, one or more disintegrants, and one or more glidants, one or more film-coating agents, one or more plasticizers, one or more pigments, and the like.

The pharmaceutical compositions (tablets) of this invention comprise usually a binder.

In more detail, the pharmaceutical compositions (tablets) of this invention comprise usually one or more fillers (e.g. D-mannitol, corn starch and/or pregelatinized starch and/or microcrystalline cellulose), a binder (e.g. copovidone), a lubricant (e.g. magnesium stearate, sodium stearyl fumarate), and a glidant (e.g. colloidal anhydrous silica).

Suitably the pharmaceutical excipients used within this invention are conventional materials such as D-mannitol, corn starch, microcrystalline cellulose, pregelatinized starch as a filler, copovidone as a binder, magnesium stearate or sodium stearyl fumarate as a lubricant, colloidal anhydrous silica as a glidant, hypromellose as a film-coating agent, propylene glycol as a plasticizer, titanium dioxide, iron oxide red/yellow/black or mixture thereof as a pigment, and talc, etc.

A typical composition according to the present invention comprises the binder copovidone (also known as copolyvidon or Kollidon VA64).

Further, a typical composition according to the present invention comprises the filler corn starch, the binder copovidone, the lubricant magnesium stearate, and the glidant colloidal anhydrous silica.

Further, a typical composition according to the present invention comprises the filler microcrystalline cellulose, the binder copovidone, the lubricant magnesium stearate or sodium stearyl fumarate, and the glidant colloidal anhydrous silica and optionally the disintegrant crospovidone or croscarmellose sodium.

Thus, in particular, the present invention is directed to a pharmaceutical composition (especially an oral solid dosage form, particularly a tablet) comprising a SGLT-2 inhibitor, metformin hydrochloride and one or more pharmaceutical excipients, particularly one or more fillers, one or more binders, one or more glidants, and/or one or more lubricants.

In more particular, the present invention is directed to a pharmaceutical composition (especially an oral solid dosage form, particularly a tablet) comprising a SGLT-2 inhibitor, metformin hydrochloride, copovidone as binder and one or more further pharmaceutical excipients.

Typical pharmaceutical compositions of this invention may comprise in the SGLT-2 inhibitor portion (% by weight of total SGLT-2 inhibitor portion):
0.1-10% SGLT-2 inhibitor,
0.1-3% SGLT-2 inhibitor,
0.4-2.2% SGLT-2 inhibitor, or
0.1-2.11% SGLT-2 inhibitor Typical pharmaceutical compositions of this invention may also comprise in the SGLT-2 inhibitor portion (% by weight of total SGLT-2 inhibitor portion):
0.1-10% SGLT-2 inhibitor,
0.1-3% SGLT-2 inhibitor,
0.4-2.2% SGLT-2 inhibitor, or
0.1-2.12 SGLT-2 inhibitor.

Typical pharmaceutical compositions of this invention may comprise one or more of the following amounts (% by weight of total coated tablet mass):
0.1-2.11% SGLT-2 inhibitor,
47-88% metformin HCl,
3.9-8.3% binder (e.g. copovidone),
2.3-8.0% filler 1 (e.g. corn starch),
0-4.4% filler 2 (e.g. pregelatinized starch),
0-33% filler 3 (e.g. D-mannitol),
0.7-1.5% lubricant (e.g. magnesium stearate),
0.05-0.5% glidant (e.g. colloidal anhydrous silica),
0.00-3.0% disintegrant (e.g. crospovidone or croscarmellose sodium).

Typical pharmaceutical compositions of this invention may comprise one or more of the following amounts (% by weight of total coated tablet mass):
0.1-2.12 SGLT-2 inhibitor,
47-88% metformin HCl,
3.9-8.3% binder (e.g. copovidone),
2.3-8.0% filler 1 (e.g. corn starch),
0-4.4% filler 2 (e.g. pregelatinized starch),
0-33% filler 3 (e.g. D-mannitol),
0.7-1.5% lubricant (e.g. magnesium stearate),
0.05-0.5% glidant (e.g. colloidal anhydrous silica),
0.00-3.0% disintegrant (e.g. crospovidone or croscarmellose sodium).

In one embodiment, the FDC formulations are chemically stable and either a) display similarity of in-vitro dissolution profiles and/or are bioequivalent to the free combination, or b) allow to adjust the in-vitro and in-vivo performance to desired levels. In a preferred embodiment the invention relates to chemically stable FDC formulations maintaining the original dissolution profiles of corresponding mono tablets of each individual entity, with a reasonable tablet size.

In one embodiment, a pharmaceutical composition of this invention is produced using fluid bed granulation.

Further details about the FDC formulations of this invention, e.g. the ingredients, ratio of ingredients (such as e.g. ratio of SGLT-2 inhibitor, metformin hydrochloride, and/or excipients), particularly with respect to special dosage forms (tablets) used within this invention as well as their preparation, become apparent to the skilled person from the disclosure hereinbefore and hereinafter (including by way of example the following examples).

Preferably the SGLT2 inhibitor is selected from a glucopyranosyl-substituted benzene derivative of the formula (I)

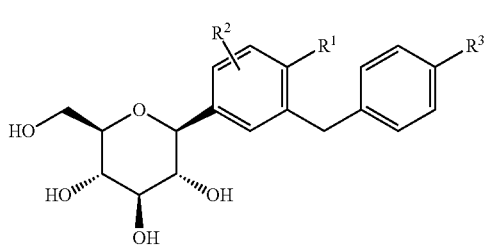

wherein $R^1$ denotes Cl, methyl or cyano; $R^2$ denotes H, methyl, methoxy or hydroxy and $R^3$ denotes ethyl, cyclopropyl, ethynyl, ethoxy, (R)-tetrahydrofuran-3-yloxy or (S)-tetrahydrofuran-3-yloxy; or a prodrug of one of the before-mentioned SGLT2 inhibitors.

In the above glucopyranosyl-substituted benzene derivatives of the formula (I) the following definitions of the substituents are preferred.

Preferably $R^1$ denotes chloro or cyano; in particular chloro.

Preferably $R^2$ denotes H.

Preferably $R^3$ denotes ethyl, cyclopropyl, ethynyl, (R)-tetrahydrofuran-3-yloxy or (S)-tetrahydrofuran-3-yloxy. Even more preferably $R^3$ denotes cyclopropyl, ethynyl, (R)-tetrahydrofuran-3-yloxy or (S)-tetrahydrofuran-3-yloxy. Most preferably $R^3$ denotes ethynyl, (R)-tetrahydrofuran-3-yloxy or (S)-tetrahydrofuran-3-yloxy.

Preferred glucopyranosyl-substituted benzene derivatives of the formula (I) are selected from the group of compounds (I.1) to (I.11):

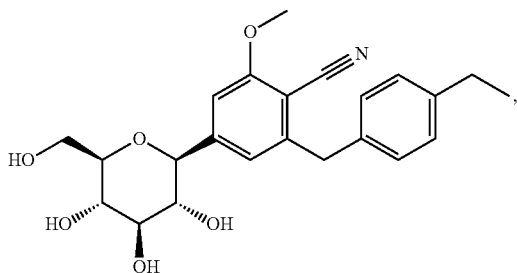

6-(4-ethylbenzyl)-4-(β-D-glucopyranos-1-yl)-2-methoxy-benzonitrile

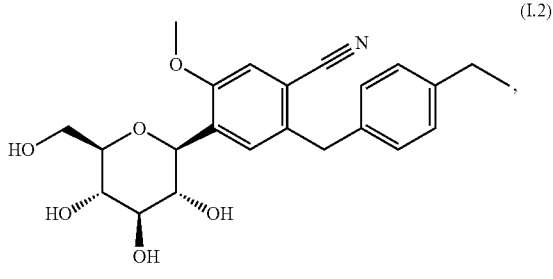

2-(4-ethylbenzyl)-4-(β-D-glucopyranos-1-yl)-5-methoxy-benzonitrile

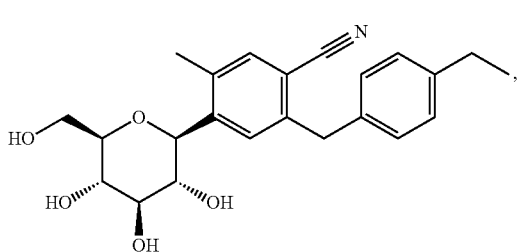

1-cyano-2-(4-ethylbenzyl)-4-(β-D-glucopyranos-1-yl)-5-methyl-benzene

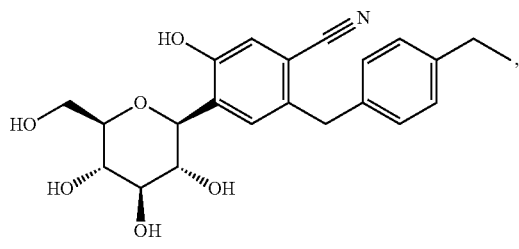

2-(4-ethylbenzyl)-4-(β-D-glucopyranos-1-yl)-5-hydroxy-benzonitrile (I.4)

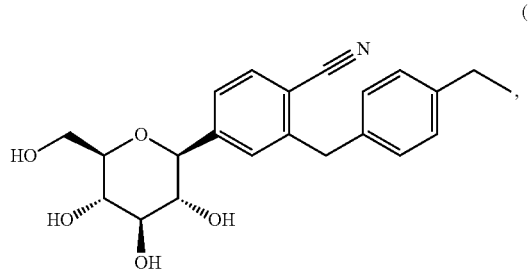

2-(4-ethyl-benzyl)-4-(β-D-glucopyranos-1-yl)-benzonitrile (I.5)

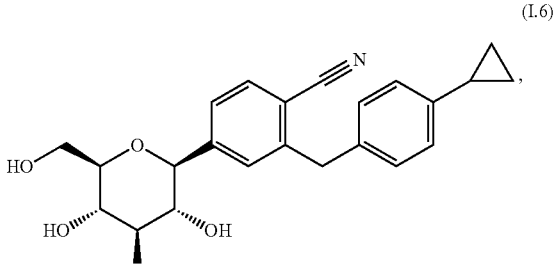

2-(4-cyclopropyl-benzyl)-4-(β-D-glucopyranos-1-yl)-benzonitrile (I.6)

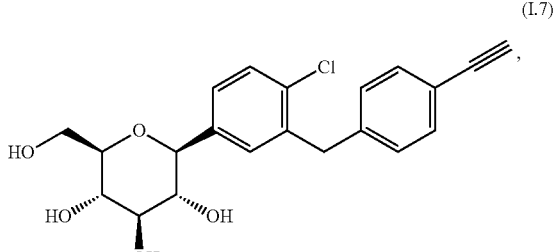

1-chloro-4-(β-D-glucopyranos-1-yl)-2-(4-ethynyl-benzyl)-benzene (I.7)

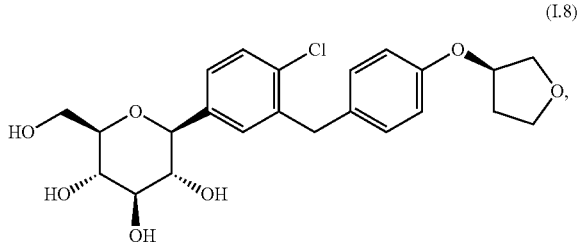

1-chloro-4-(β-D-glucopyranos-1-yl)-2-[4-((R)-tetrahydrofuran-3-yloxy)-benzyl]-benzene (I.8)

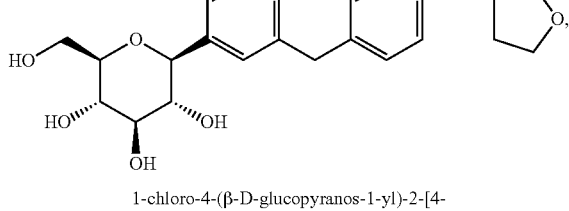

1-chloro-4-(β-D-glucopyranos-1-yl)-2-[4-((S)-tetrahydrofuran-3-yloxy)-benzyl]-benzene (I.9)

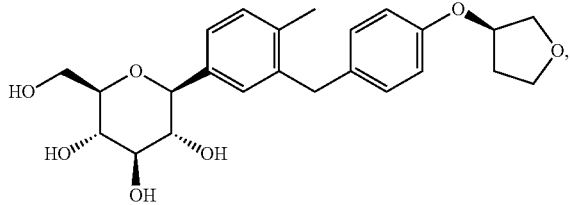

1-methyl-2-[4-((R)-tetrahydrofuran-3-yloxy)-benzyl]-4-(β-D-glucopyranos-1-yl)-benzene (I.10)

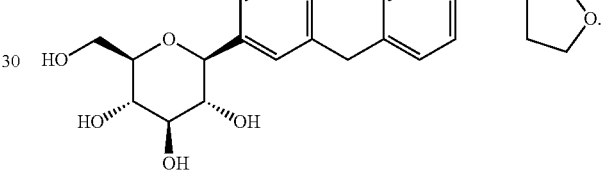

1-methyl-2-[4-((S)-tetrahydrofuran-3-yloxy)-benzyl]-4-(β-D-glucopyranos-1-yl)-benzene (I.11)

Even more preferred glucopyranosyl-substituted benzene derivatives of the formula (I) are selected from the compounds (I.6), (I.7), (I.8), (I.9) and (I.11).

Even more preferred glucopyranosyl-substituted benzene derivatives of the formula (I) are selected from the compounds (I.8) and (I.9), or a crystalline form (I.9X) of compound (I.9).

The pharmaceutical compositions according to the invention allow a high content uniformity and an effective production with regard to time and costs of pharmaceutical dosage forms, such as tablets and capsules. Furthermore, in one embodiment, these pharmaceutical dosage forms are in particular tablets.

Therefore in another aspect the present invention provides a pharmaceutical dosage form comprising a pharmaceutical composition according to the invention. In one aspect, the pharmaceutical dosage form according to the invention is a solid pharmaceutical dosage form, for example a solid pharmaceutical dosage form for oral administration.

In another aspect, the present invention provides a process for the preparation of a pharmaceutical dosage form according to the invention comprising one or more granulation processes wherein the active pharmaceutical ingredient together with one or more excipients is granulated.

It can be found that a pharmaceutical composition comprising a SGLT2 inhibitor and partner drug as defined hereinafter can advantageously be used for preventing, slowing progression of, delaying or treating a metabolic disorder, in particular for improving glycemic control in patients. This opens up new therapeutic possibilities in the treatment and prevention of type 2 diabetes mellitus, overweight, obesity, complications of diabetes mellitus and of neighboring disease states.

Therefore, in a first aspect the present invention provides a method for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome in a patient in need thereof characterized in that a pharmaceutical composition or a pharmaceutical dosage form of the present invention is administered to the patient.

According to another aspect of the invention, there is provided a method for improving glycemic control and/or for reducing of fasting plasma glucose, of postprandial plasma glucose and/or of glycosylated hemoglobin HbA1c in a patient in need thereof characterized in that a pharmaceutical composition or a pharmaceutical dosage form of the present invention is administered to the patient.

The pharmaceutical composition according to this invention may also have valuable disease-modifying properties with respect to diseases or conditions related to impaired glucose tolerance (IGT), impaired fasting blood glucose (IFG), insulin resistance and/or metabolic syndrome.

According to another aspect of the invention, there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that a pharmaceutical composition or a pharmaceutical dosage form of the present invention is administered to the patient.

As by the use of a pharmaceutical composition according to this invention, an improvement of the glycemic control in patients in need thereof is obtainable, also those conditions and/or diseases related to or caused by an increased blood glucose level may be treated.

According to another aspect of the invention, there is provided a method for preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis, in a patient in need thereof characterized in that a pharmaceutical composition or a pharmaceutical dosage form of the present invention is administered to the patient. In particular one or more aspects of diabetic nephropathy such as hyperperfusion, proteinuria and albuminuria may be treated, their progression slowed or their onset delayed or prevented. The term "tissue ischaemia" particularly comprises diabetic macroangiopathy, diabetic microangiopathy, impaired wound healing and diabetic ulcer. The terms "micro- and macrovascular diseases" and "micro- and macrovascular complications" are used interchangeably in this application.

By the administration of a pharmaceutical composition according to this invention and due to the activity of the SGLT2 inhibitor excessive blood glucose levels are not converted to insoluble storage forms, like fat, but excreted through the urine of the patient. Therefore, no gain in weight or even a reduction in body weight is the result.

According to another aspect of the invention, there is provided a method for reducing body weight or preventing an increase in body weight or facilitating a reduction in body weight in a patient in need thereof characterized in that a pharmaceutical composition or a pharmaceutical dosage form of the present invention is administered to the patient.

The pharmacological effect of the SGLT2 inhibitor in the pharmaceutical composition according to this invention is independent of insulin. Therefore, an improvement of the glycemic control is possible without an additional strain on the pancreatic beta cells. By an administration of a pharmaceutical composition according to this invention a beta-cell degeneration and a decline of beta-cell functionality such as for example apoptosis or necrosis of pancreatic beta cells can be delayed or prevented. Furthermore, the functionality of pancreatic cells can be improved or restored, and the number and size of pancreatic beta cells increased. It may be shown that the differentiation status and hyperplasia of pancreatic beta-cells disturbed by hyperglycemia can be normalized by treatment with a pharmaceutical composition according to this invention.

According to another aspect of the invention, there is provided a method for preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion in a patient in need thereof characterized in that a pharmaceutical composition or a pharmaceutical dosage form of the present invention is administered to the patient.

By the administration of a pharmaceutical composition according to the present invention, an abnormal accumulation of fat in the liver may be reduced or inhibited. Therefore, according to another aspect of the present invention, there is provided a method for preventing, slowing, delaying or treating diseases or conditions attributed to an abnormal accumulation of liver fat in a patient in need thereof characterized in that an SGLT2 inhibitor as defined hereinbefore and hereinafter is administered to the patient. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

As a result thereof, another aspect of the invention provides a method for maintaining and/or improving the insulin sensitivity and/or for treating or preventing hyperinsulinemia and/or insulin resistance in a patient in need thereof characterized in that a pharmaceutical composition or a pharmaceutical dosage form of the present invention is administered to the patient.

According to another aspect of the invention there is provided the use of a pharmaceutical composition or a pharmaceutical dosage form of the present invention for the manufacture of a medicament for preventing, slowing the progression of, delaying or treating a metabolic disorder selected from the group consisting of type 1 diabetes mellitus, type 2 diabetes mellitus, impaired glucose tolerance (IGT), impaired fasting blood glucose (IFG), hyperglycemia, postprandial hyperglycemia, overweight, obesity and metabolic syndrome; or improving glycemic control and/or for reducing of fasting plasma glucose, of postprandial plasma glucose and/or of glycosylated hemoglobin HbA1c; or preventing, slowing, delaying or reversing progression from impaired glucose tolerance (IGT), impaired fasting blood glucose (IFG), insulin resistance and/or from metabolic syndrome to type 2 diabetes mellitus; or preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis; or reducing body weight or preventing an increase in body weight or facilitating a reduction in body weight; or preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or preventing, slowing, delaying or treating diseases or conditions attributed to an abnormal accumulation of liver fat; or maintaining and/or improving the insulin sensitivity and/or for treating or preventing hyperinsulinemia and/or insulin resistance;

in a patient in need thereof characterized in that the SGLT2 inhibitor is administered, as defined hereinbefore and hereinafter.

According to another aspect of the invention, there is provided the use of a pharmaceutical composition or a pharmaceutical dosage form of the present invention according to the present invention for the manufacture of a medicament for a therapeutic and preventive method as described hereinbefore and hereinafter.

Definitions

The term "active ingredient" of a pharmaceutical composition according to the present invention means the SGLT2 inhibitor according to the present invention. An "active ingredient is also sometimes referred to herein as an "active substance".

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 110 mg/dL (6.11 mmol/L). The word "fasting" has the usual meaning as a medical term.

The term "hyperglycemia" is defined as the condition in which a subject has a fasting blood glucose concentration above the normal range, greater than 110 mg/dL (6.11 mmol/L). The word "fasting" has the usual meaning as a medical term.

The term "hypoglycemia" is defined as the condition in which a subject has a blood glucose concentration below the normal range of 60 to 115 mg/dL (3.3 to 6.3 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$HOMA\text{-}IR = [fasting\ serum\ insulin(\mu U/mL)] \times [fasting\ plasma\ glucose(mmol/L)/22.5]$$

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homeostasis a person needs 2-3 times as much insulin as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range ≥100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP ≥130 or DBP ≥85)
5. Fasting blood glucose ≥110 mg/dL The NCEP definitions have been validated (Laaksonen D E, et al. *Am J. Epidemiol.* (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The term "SGLT2 inhibitor" in the scope of the present invention relates to compounds, in particular to glucopyranosyl-derivatives, i.e. compounds having a glucopyranosyl-moiety, which show an inhibitory effect on the sodium-glucose transporter 2 (SGLT2), in particular the human SGLT2. The inhibitory effect on hSGLT2 measured as IC50 is preferably below 1000 nM, even more preferably below 100 nM, most preferably below 50 nM. The inhibitory effect on hSGLT2 can be determined by methods known in the literature, in particular as described in the application WO 2005/092877 or WO 2007/093610 (pages 23/24), which are incorporated herein by reference in its entirety. The term "SGLT2 inhibitor" also comprises any pharmaceutically acceptable salts thereof, hydrates and solvates thereof, including the respective crystalline forms.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventively treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the before mentioned types of tablets may be without or with one or more coatings. The term "tablet" also comprises mini, melt, chewable, effervescent and orally disintegrating tablets.

The terms "pharmacopoeia" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

DETAILED DESCRIPTION

The aspects according to the present invention, in particular the pharmaceutical compositions, methods and uses, refer to SGLT2 inhibitors as defined hereinbefore and hereinafter.

Preferably the SGLT2 inhibitor is selected from a glucopyranosyl-substituted benzene derivative of the formula (I)

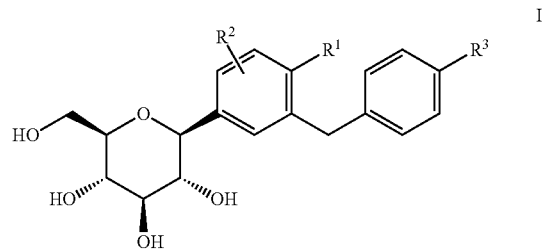

wherein $R^1$ denotes Cl, methyl or cyano; $R^2$ denotes H, methyl, methoxy or hydroxy and $R^3$ denotes ethyl, cyclopropyl, ethynyl, ethoxy, (R)-tetrahydrofuran-3-yloxy or (S)-tetrahydrofuran-3-yloxy; or a prodrug of one of the before-mentioned SGLT2 inhibitors.

Compounds of the formula (I) and methods of their synthesis are described for example in the following patent applications: WO 2005/092877, WO 2006/117360, WO 2006/117359, WO 2006/120208, WO 2006/064033, WO 2007/031548, WO 2007/093610, WO 2008/020011, WO 2008/055870.

In the above glucopyranosyl-substituted benzene derivatives of the formula (I) the following definitions of the substituents are preferred.

Preferably $R^1$ denotes chloro or cyano; in particular chloro.

Preferably $R^2$ denotes H.

Preferably $R^3$ denotes ethyl, cyclopropyl, ethynyl, (R)-tetrahydrofuran-3-yloxy or (S)-tetrahydrofuran-3-yloxy. Even more preferably $R^3$ denotes cyclopropyl, ethynyl, (R)-tetrahydrofuran-3-yloxy or (S)-tetrahydrofuran-3-yloxy. Most preferably $R^3$ denotes ethynyl, (R)-tetrahydrofuran-3-yloxy or (S)-tetrahydrofuran-3-yloxy.

Preferred glucopyranosyl-substituted benzene derivatives of the formula (I) are selected from the group of compounds (I.1) to (I.11):

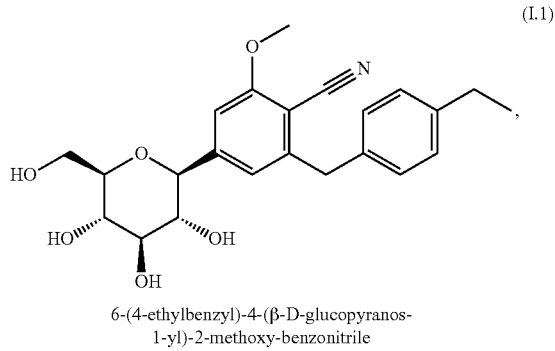

6-(4-ethylbenzyl)-4-(β-D-glucopyranos-1-yl)-2-methoxy-benzonitrile

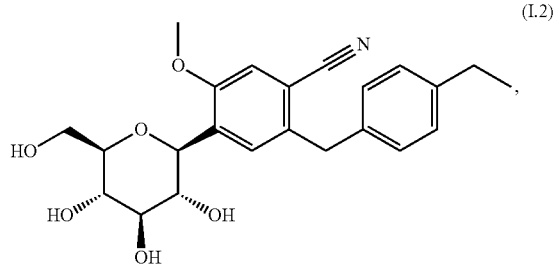

2-(4-ethylbenzyl)-4-(β-D-glucopyranos-1-yl)-5-methoxy-benzonitrile

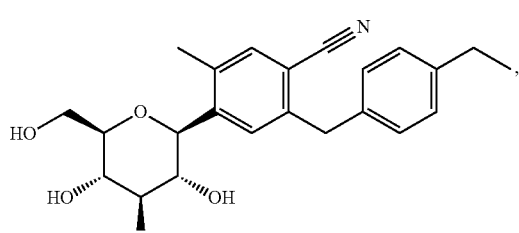

1-cyano-2-(4-ethylbenzyl)-4-(β-D-glucopyranos-1-yl)-5-methyl-benzene

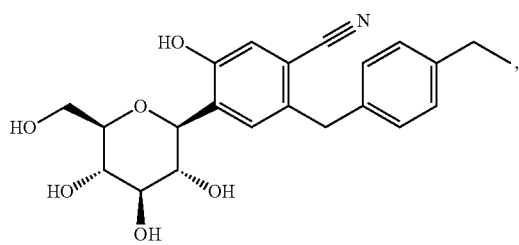

2-(4-ethylbenzyl)-4-(β-D-glucopyranos-1-yl)-5-hydroxy-benzonitrile (I.5)

2-(4-ethyl-benzyl)-4-(β-D-glucopyranos-1-yl)-benzonitrile

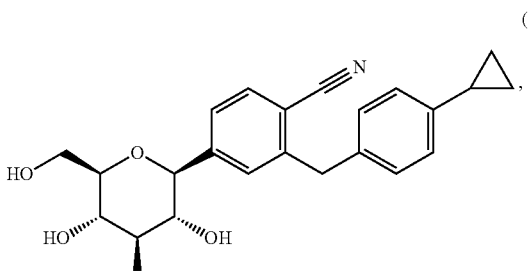

2-(4-cyclopropyl-benzyl)-4-(β-D-glucopyranos-1-yl)-benzonitrile

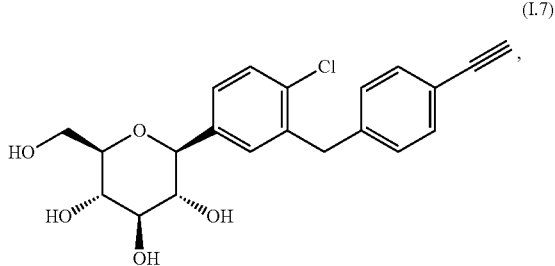

1-chloro-4-(β-D-glucopyranos-1-yl)-2-(4-ethynyl-benzyl)-benzene

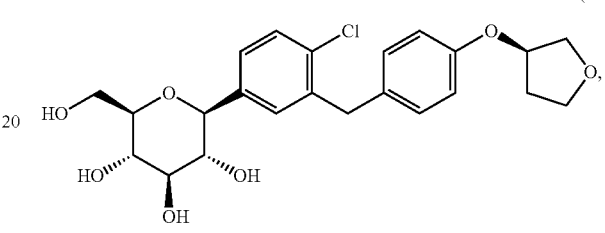

1-chloro-4-(β-D-glucopyranos-1-yl)-2-[4-((R)-tetrahydrofuran-3-yloxy)-benzyl]-benzene

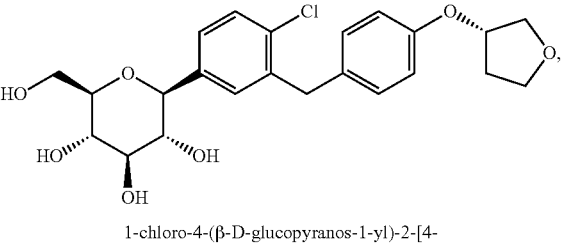

1-chloro-4-(β-D-glucopyranos-1-yl)-2-[4-((S)-tetrahydrofuran-3-yloxy)-benzyl]-benzene

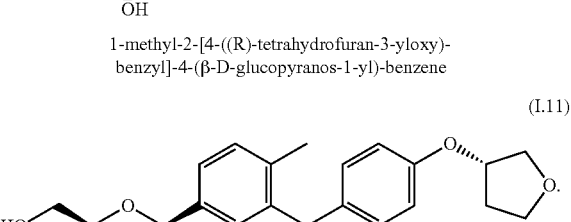

1-methyl-2-[4-((R)-tetrahydrofuran-3-yloxy)-benzyl]-4-(β-D-glucopyranos-1-yl)-benzene

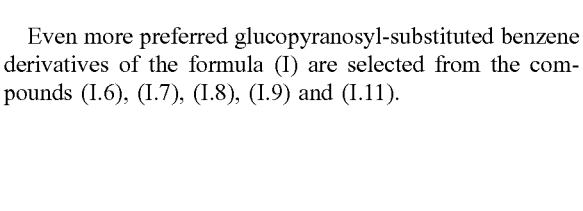

1-methyl-2-[4-((S)-tetrahydrofuran-3-yloxy)-benzyl]-4-(β-D-glucopyranos-1-yl)-benzene Even more preferred glucopyranosyl-substituted benzene derivatives of the formula (I) are selected from the compounds (I.6), (I.7), (I.8), (I.9) and (I.11).

Even more preferred glucopyranosyl-substituted benzene derivatives of the formula (I) are selected from the compounds (I.8) and (I.9).

According to this invention, it is to be understood that the definitions of the above listed glucopyranosyl-substituted benzene derivatives of the formula (I) also comprise their hydrates, solvates and polymorphic forms thereof, and pro-drugs thereof. With regard to the preferred compound (I.7) an advantageous crystalline form is described in the international patent application WO 2007/028814 which hereby is incorporated herein in its entirety. With regard to the preferred compound (I.8), an advantageous crystalline form is described in the international patent application WO 2006/117360 which hereby is incorporated herein in its entirety. With regard to the preferred compound (I.9) an advantageous crystalline form is described in the international patent application WO 2006/117359 which hereby is incorporated herein in its entirety. With regard to the preferred compound (I.11) an advantageous crystalline form is described in the international patent application WO 2008/049923 which hereby is incorporated herein in its entirety. These crystalline forms possess good solubility properties which enable a good bioavailability of the SGLT2 inhibitor. Furthermore, the crystalline forms are physico-chemically stable and thus provide a good shelf-life stability of the pharmaceutical composition.

For avoidance of any doubt, the disclosure of each of the foregoing documents cited above in connection with the specified SGLT2 inhibitors is specifically incorporated herein by reference in its entirety.

A preferred crystalline form (I.9X) of the compound (I.9) can be characterized by an X-ray powder diffraction pattern that comprises peaks at 18.84, 20.36 and 25.21 degrees 2 Θ (±0.1 degrees 2Θ), wherein said X-ray powder diffraction pattern (XRPD) is made using $CuK_{\alpha 1}$ radiation.

In particular said X-ray powder diffraction pattern comprises peaks at 14.69, 18.84, 19.16, 19.50, 20.36 and 25.21 degrees 2Θ (±0.1 degrees 2Θ), wherein said X-ray powder diffraction pattern is made using $CuK_{\alpha 1}$ radiation.

In particular said X-ray powder diffraction pattern comprises peaks at 14.69, 17.95, 18.43, 18.84, 19.16, 19.50, 20.36, 22.71, 23.44, 24.81, 25.21 and 25.65 degrees 2Θ (±0.1 degrees 2Θ), wherein said X-ray powder diffraction pattern is made using $CuK_{\alpha 1}$ radiation.

More specifically, the crystalline form (I.9X) is characterised by an X-ray powder diffraction pattern, made using $CuK_{\alpha 1}$ radiation, which comprises peaks at degrees 2Θ (±0.1 degrees 2Θ) as contained in Table 1.

TABLE 1

X-ray powder diffraction pattern of the crystalline form (I.9X) (only peaks up to 30° in 2 Θ are listed):

| 2 Θ [°] | d-value [Å] | Intensity $I/I_0$ [%] |
|---|---|---|
| 4.46 | 19.80 | 8 |
| 9.83 | 8.99 | 4 |
| 11.68 | 7.57 | 4 |
| 13.35 | 6.63 | 14 |
| 14.69 | 6.03 | 42 |
| 15.73 | 5.63 | 16 |
| 16.20 | 5.47 | 8 |
| 17.95 | 4.94 | 30 |
| 18.31 | 4.84 | 22 |
| 18.43 | 4.81 | 23 |
| 18.84 | 4.71 | 100 |
| 19.16 | 4.63 | 42 |
| 19.50 | 4.55 | 31 |

TABLE 1-continued

X-ray powder diffraction pattern of the crystalline form (I.9X) (only peaks up to 30° in 2 Θ are listed):

| 2 Θ [°] | d-value [Å] | Intensity $I/I_0$ [%] |
|---|---|---|
| 20.36 | 4.36 | 74 |
| 20.55 | 4.32 | 13 |
| 21.18 | 4.19 | 11 |
| 21.46 | 4.14 | 13 |
| 22.09 | 4.02 | 19 |
| 22.22 | 4.00 | 4 |
| 22.71 | 3.91 | 28 |
| 23.44 | 3.79 | 27 |
| 23.72 | 3.75 | 3 |
| 24.09 | 3.69 | 3 |
| 24.33 | 3.66 | 7 |
| 24.81 | 3.59 | 24 |
| 25.21 | 3.53 | 46 |
| 25.65 | 3.47 | 23 |
| 26.40 | 3.37 | 2 |
| 26.85 | 3.32 | 8 |
| 27.26 | 3.27 | 17 |
| 27.89 | 3.20 | 2 |
| 28.24 | 3.16 | 3 |
| 29.01 | 3.08 | 4 |
| 29.41 | 3.03 | 18 |

Even more specifically, the crystalline form (I.9X) is characterised by an X-ray powder diffraction pattern, made using $CuK_{\alpha 1}$ radiation, which comprises peaks at degrees 2Θ (±0.1 degrees 2Θ) as shown in FIG. 1 of WO 2006/117359.

Furthermore the crystalline form (I.9X) is characterised by a melting point of about 151° C.±5° C. (determined via DSC; evaluated as onset-temperature; heating rate 10 K/min). The obtained DSC curve is shown in FIG. 2 of WO 2006/117359.

The X-ray powder diffraction patterns are recorded, within the scope of the present invention, using a STOE-STADI P-diffractometer in transmission mode fitted with a location-sensitive detector (OED) and a Cu-anode as X-ray source ($CuK\alpha 1$ radiation, $\lambda=1,54056$ Å, 40 kV, 40 mA). In the Table 1 above the values "2Θ[°]" denote the angle of diffraction in degrees and the values "d [Å]" denote the specified distances in Å between the lattice planes. The intensity shown in the FIG. 1 of WO 2006/117359 is given in units of cps (counts per second).

In order to allow for experimental error, the above described 2Θ values should be considered accurate to ±0.1 degrees 2Θ, in particular ±0.05 degrees 2Θ. That is to say, when assessing whether a given sample of crystals of the compound (I.9) is the crystalline form in accordance with the invention, a 2Θ value which is experimentally observed for the sample should be considered identical with a characteristic value described above if it falls within ±0.1 degrees 2Θ of the characteristic value, in particular if it falls within ±0.05 degrees 2Θ of the characteristic value.

The melting point is determined by DSC (Differential Scanning calorimetry) using a DSC 821 (Mettler Toledo).

In one embodiment, a pharmaceutical composition or dosage form according to the present invention comprises the compound (I.9), wherein at least 50% by weight of the compound (I.9) is in the form of its crystalline form (I.9X) as defined hereinbefore. Preferably in said composition or dosage form at least 80% by weight, more preferably at least 90% by weight of the compound (I.9) is in the form of its crystalline form (I.9X) as defined hereinbefore.

The preferred dosage range of the SGLT2 inhibitor is in the range from 0.5 mg to 200 mg, even more preferably from 1 to 100 mg, most preferably from 1 to 50 mg per day. The oral administration is preferred. Therefore, a pharmaceutical composition of the present invention may comprise the hereinbefore mentioned amounts, in particular from 0.5 to 50 mg, preferably 1 to 25 mg, even more preferably 2.5 to 12.5 mg. Particular dosage strengths for use in the present invention (e.g. per tablet or capsule) are for example 0.5, 1, 1.25, 2, 2.5, 5, 7.5, 10, 12.5, 15, 20, 25 or 50 mg of the SGLT2 inhibitor, for example a compound of the formula (I), in particular of the compound (I.9) or its crystalline form (I.9X). Particularly preferred dosage strengths (e.g. per tablet or capsule) are for example 0.5, 1, 1.25, 2.5, 5, 10, or 12.5, mg of the SGLT2 inhibitor, for example a compound of the formula (I), in particular of the compound (I.9) or its crystalline form (I.9X).

In one aspect, partner drugs to be combined with the SGLT-2 within the pharmaceutical compositions according to this invention are biguanides (e.g. metformin such as metformin hydrochloride).

A preferred partner drug within the meaning of this invention is metformin, particularly metformin hydrochloride (1,1-dimethylbiguanide hydrochloride or metformin HCl).

The biguanide antihyperglycemic agent metformin is disclosed in U.S. Pat. No. 3,174,901. The preparation of metformin (dimethyldiguanide) and its hydrochloride salt is state of the art and was disclosed first by Emil A. Werner and James Bell, J. Chem. Soc. 121, 1922, 1790-1794. Other pharmaceutically acceptable salts of metformin can be found in U.S. application Ser. No. 09/262,526 filed Mar. 4, 1999 or U.S. Pat. No. 3,174,901. It is preferred that the metformin employed herein be the metformin hydrochloride salt.

Metformin is usually given in doses varying from about 250 mg to 3000 mg, particularly from 500 mg to 2000 mg up to 2500 mg per day using various dosage regimens.

A dosage range of the partner drug metformin is usually from 100 mg to 500 mg or 200 mg to 850 mg (1-3 times a day), or from 300 mg to 1000 mg once or twice a day.

The unit dosage strengths of the metformin hydrochloride for use in the present invention may be from 100 mg to 2000 mg or from 100 mg to 1500 mg, preferably from 250 mg to 1000 mg. Particular dosage strengths may be 250, 500, 625, 750, 850 and 1000 mg of metformin hydrochloride. These unit dosage strengths of metformin hydrochloride represent the dosage strengths approved in the US for marketing to treat type 2 diabetes. More particular unit dosage strengths of metformin hydrochloride for incorporation into the fixed dose combination pharmaceutical compositions of the present invention are 500, 850 and 1000 mg of metformin hydrochloride.

In a further aspect of the present invention, the present invention provides a pharmaceutical composition, formulation, blend or dosage form of this invention which is substantially free of or only marginally comprises impurities and/or degradation products; that means, for example, that the composition, formulation, blend or dosage from includes about <5%, or about <4%, or about <3%, or less than about 2%, preferably less than about 1%, more preferably less than about 0.5%, even more preferably less than about 0.2% of any individual or total impurity or degradation product(s) by total weight.

Dosage forms for the FDC formulations of this invention:

Another purpose of this invention is to develop the FDC formulations of this invention with a reasonable tablet size, with good tablet properties (e.g. stability, hardness, friability, disintegration, dissolution profile, content uniformity and the like).

Thus, it has been found that suitable dosage forms for the FDC formulations of this invention are film-coated tablets (film-coating for drug loading, such as particularly SGLT-2 inhibitor drug loading by film coating on tablet cores containing the partner drug), mono-layer tablets, bi-layer tablets, tri-layer tablets and press-coated tablets (e.g. tablet-in-tablet or bull's eye tablet with SGLT-2 inhibitor core), which dosage forms are good measures to achieve the goal under consideration of desired pharmaceutical profiles and characteristics of a SGLT-2 inhibitor and a partner drug used.

Said dosage forms have been found to be applicable to the FDC formulations either keeping the original dissolution profiles of each mono tablet or adjusting the profiles to desired levels, and a reasonable tablet size.

A typical mono-layer tablet of this invention comprises a SGLT-2 inhibitor, metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

In one embodiment of the present invention, the present invention is directed to an oral solid pharmaceutical composition, preferably a tablet, particularly a mono-layer tablet, wherein one or more of the following applies:

the percentage of metformin hydrochloride is about 84% by weight of total tablet core,
the percentage of SGLT-2 inhibitor is about 0.1%-2.12%, e.g. 0.1%-2.11% by weight of total tablet core,
the tablet crushing strength is higher than or equal 100 N,
the tablet friability is lower than or equal 0.5%,
the tablet core weight is from about 560 to about 1180 mg, and
the tablet disintegration time is lower than or equal 15 min.

In one embodiment, the SGLT-2 inhibitor a compound of the formula (I), in particular of the compound (I.9) or its crystalline form (I.9X).

In a preferred embodiment of the present invention, the present invention is directed to an oral solid pharmaceutical composition, preferably a tablet, particularly a mono-layer tablet comprising or made from
a compound of the formula (I), for example of the formula (I.9) or its crystalline form (I.9X), e.g. in an amount of 0.5, 1, 1.25, 2.5, 5, 10 or 12.5 mg,
metformin, particularly metformin hydrochloride, e.g. in an amount of 500 mg, 850 mg or 1000 mg,
and one or more pharmaceutical excipients, particularly one or more fillers (e.g. corn starch), one or more binders (e.g. copovidone), one or more glidants (e.g. colloidal anhydrous silica) and/or one or more lubricants (e.g. magnesium stearate),
as well as, optionally, a film coat e.g. comprising one or more film-coating agents (e.g. hypromellose), one or more plasticizers (e.g. propylene glycol, polyethylene glycol or triethyl citrate), one or more pigments (e.g. titanium dioxide, iron oxide red/yellow/black or mixture thereof) and/or one or more glidants (e.g. talc).

In a further aspect of the present invention, the present invention provides methods of manufacturing of the compositions, formulations, blends or dosage forms of this invention, such as e.g. by using methods known to one skilled in the art and/or in a manner as described herein, for example they may be obtained by processes comprising using (e.g. mixing, combining, blending and/or composing) the components and/or ingredients, or pre-mixtures thereof, mentioned hereinbefore and hereinafter, as well as the present invention further provides compositions, formulations, blends or dosage forms obtainable by these methods or processes and/or obtainable from the components, ingredients, pre-mixtures and/or mixtures mentioned hereinbefore and hereinafter.

A method of manufacturing a tablet of this invention comprises tabletting (e.g. compression) of one or more final blends in form of granules. Granules of the (final) blend(s) according to this invention may be prepared by methods well-known to one skilled in the art (e.g. high shear wet granulation or fluid bed granulation). Granules according to this invention as well as details of granulation processes (including their separate steps) for the preparation of granules of this invention are described by way of example in the following examples.

An illustrative granulation process for the preparation of granules comprising the mono-layer composition comprises
i.) combining (e.g. dissolving or dispersing) a binder (e.g. copovidone) and, optionally, the SGLT-2 inhibitor (e.g. a compound of the formula (I), for example of the formula (I.9) or its crystalline form (I.9X)) in a solvent or mixture of solvents such as purified water at ambient temperature to produce a granulation liquid;
ii.) blending metformin HCl, a filler (e.g. corn starch) and, optionally, the SGLT-2 inhibitor in a suitable mixer (e.g. fluid-bed granulator) to produce a pre-mix;
wherein the SGLT-2 inhibitor may be included either in the granulation liquid obtained in i.) or in the pre-mix obtained in ii.), preferably the SGLT-2 inhibitor is dispersed in the granulation liquid and is absent in the pre-mix;
iii.) spraying the granulation-liquid into the pre-mix and granulating the mixture for example in a fluid-bed granulator, preferably under dry condition;
iv.) drying the granulate, e.g. at about 70° C. inlet air temperature until the desired loss on drying value in the range of 1-3%, for example 0.8-2%, is obtained;
v.) delumping the dried granulate for example by sieving through a sieve with a mesh size of 0.5 to 1.0 mm;
vi.) blending the sieved granulate and preferably sieved glidant (e.g. colloidal anhydrous silica) in a suitable blender;
vii.) adding preferably sieved lubricant (e.g. magnesium stearate) to the granulate for final blending for example in the free-fall blender.

Preferentially, a mono-layer tablet according to this invention comprises or is obtainable from a mixture comprising the SGLT-2 inhibitor and metformin.

A typical bi-layer tablet of this invention comprises
a SGLT-2 inhibitor portion comprising a SGLT-2 inhibitor, one or more fillers (such as e.g. D-mannitol, pregelatinized starch and corn starch), one or more binders (such as e.g. copovidone) and one or more lubricants (such as e.g. magnesium stearate), and
a metformin HCl portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

A typical press-coated tablet (tablet-in-tablet or bull's eye tablet) of this invention comprises a SGLT-2 inhibitor core portion comprising a SGLT-2 inhibitor, one or more fillers (such as e.g. D-mannitol, pregelatinized starch and corn starch), one or more binders (such as e.g. copovidone) and one or more lubricants (such as e.g. magnesium stearate), and
a metformin HCl portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate).

A typical film-coated tablet (the SGLT-2 inhibitor coating on metformin HCl tablet, i.e. drug layering by film-coating for drug loading) of this invention comprises
a metformin HCl core portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate),
wherein said core portion is seal-coated with a film coat comprising one or more film-coating agents (such as e.g. hypromellose), one or more plasticizers (such as e.g. propylene glycol, Macrogol 400, Macrogol 6000, Macrogol 8000), one or more pigments (such as e.g. titanium dioxide, iron oxide red/yellow/black or mixture thereof) and one or more glidants (such as e.g. talc);
and
a SGLT-2 inhibitor layer comprising a SGLT-2 inhibitor, one or more film-coating agents (such as e.g. hypromellose) and one or more plasticizers (such as e.g. propylene glycol, Macrogol 400, Macrogol 6000, or Macrogol 8000, triethyl citrate).

Another typical film-coated tablet (the SGLT-2 inhibitor coating on metformin HCl tablet, i.e. drug layering by film-coating for drug loading) of this invention comprises a metformin HCl core portion comprising metformin hydrochloride, one or more fillers (such as e.g. corn starch), one or more binders (such as e.g. copovidone), one or more glidants (such as e.g. colloidal anhydrous silica) and one or more lubricants (such as e.g. magnesium stearate),
wherein said core portion is seal-coated with a film coat comprising one or more film-coating agents (such as e.g. hypromellose), one or more plasticizers (such as e.g. propylene glycol, Macrogol 400, Macrogol 6000, or Macrogol 8000, triethyl citrate), one or more pigments (such as e.g. titanium dioxide, iron oxide red/yellow/black or mixture thereof) and one or more glidants (such as e.g. talc);
and
a SGLT-2 inhibitor layer comprising a SGLT-2 inhibitor, one or more film-coating agents (such as e.g. hypromellose) and one or more plasticizers (such as e.g. propylene glycol, Macrogol 400, Macrogol 6000, or Macrogol 8000, triethyl citrate).

Preferably, these abovementioned tablets (mono-, bi-layer, press-coated and drug-coated tablets) are further over-coated with a final film coat, which comprises a film-coating agent (such as e.g. hypromellose), a plasticizer (such as e.g. propylene glycol, Macrogol 400, Macrogol 6000, or Macrogol 8000, triethyl citrate), pigments (such as e.g. titanium dioxide, iron oxide red/yellow/black or mixture thereof) and a glidant (such as e.g. talc). Typically this additional film over-coat may represent 1-4%, preferentially 1-2%, of the total mass of the composition.

A pharmaceutical composition or dosage form according to the present invention may be an immediate release pharmaceutical composition or dosage form, or a time-release pharmaceutical composition or dosage form.

Pharmaceutical immediate release dosage forms of this invention preferably have dissolution properties such that after 45 minutes for each of the active ingredients at least 75%, even more preferably at least 90% by weight of the respective active ingredient is dissolved. In a particular embodiment, after 30 minutes for each of the active ingredients especially of the mono-layer tablet according to this invention (including tablet core and film-coated tablet) at least 70-75% (preferably at least 80%) by weight of the respective active ingredient is dissolved. In a further embodiment, after 15 minutes for each of the active ingredients especially of the mono-layer tablet according to this invention (including tablet core and film-coated tablet) at least 55-60% by weight of the respective active ingredient is dissolved. The dissolution properties can be determined in standard dissolution tests, e.g. according to standard pharmacopoeias (e.g. using paddle method with agitation speed of 50 or 75 or 100 rpm, dissolution medium pH 6.8 at a temperature of 37° C.).

A time-release dosage form refers to a formula that is not an immediate release dosage form. In a time-release dosage form the release of the active ingredient is slow and occurs over time. Time-release dosage forms are also known as sustained-release (SR), sustained-action (SA), extended-release (ER, XR, or XL), time-release or timed-release, controlled-release (CR), modified release (MR), or continuous-release (CR or Contin), In one aspect, a time-release dosage form may be a bi-layer tablet in which one or more of the active ingredients is released slowly. In one aspect, in a pharmaceutical composition and pharmaceutical dosage form according to the invention the SGLT-2 inhibitor, for example a compound of the formula (I), for example of the formula (I.9) or its crystalline form (I.9X), or the partner drug, for example a biguanide, for example metformin such as metformin hydrochloride, is time-release.

In another aspect, in a pharmaceutical composition and pharmaceutical dosage form according to the invention the SGLT-2 inhibitor, for example a compound of the formula (I), for example of the formula (I.9) or its crystalline form (I.9X), and the partner drug, for example a biguanide, for example metformin such as metformin hydrochloride, are time-release.

In the pharmaceutical compositions and pharmaceutical dosage forms according to the invention the SGLT-2 inhibitor, for example a compound of the formula (I), for example of the formula (I.9) or its crystalline form (I.9X), preferably has a particle size distribution (preferably by volume) such that at least 90% of the respective active pharmaceutical ingredient has a particle size smaller than 200 µm, i.e. X90 <200 µm, more preferably X90≤150 µm. More preferably the particle size distribution is such that X90≤100 µm, more preferably X90≤90 µm, even more preferably X90≤75 µm. In addition the particle size distribution is preferably such that X90>1 µm, more preferably X90≥5 µm, most preferably X90≥10 µm. Therefore preferred particle size distributions are such that 1 µm<X90 <200 µm, particularly 1 µm<X90≤150 µm, more preferably 5 µm≤X90≤150 µm, even more preferably 5 µm≤X90≤100 µm, even more preferably 10 µm≤X90≤100 µm. A preferred example of a particle size distribution of the SGLT-2 inhibitor is 20 µm≤X90≤50 µm. It can be found that a pharmaceutical composition comprising compound (I.9), or crystalline form (I.9X) of compound (I.9) with a particle size distribution as indicated hereinbefore shows desired properties (e.g. with regard to dissolution, content uniformity, production, or the like). The indicated particle size properties are determined by laser-diffraction method, in particular low angle laser light scattering, i.e. Fraunhofer diffraction. Alternatively, the particle size properties can be also determined by microscopy (e.g. electron microscopy or scanning electron microscopy). The results of the particle size distribution determined by different techniques can be correlated with one another.

Optimized formulation of metformin HCl portion:

Another purpose of this invention is to provide improved formulations of the metformin HCl portion of the pharmaceutical compositions according to this invention.

For the metformin HCl part a high drug load is advantageous to be achieved as a pre-requisite for a reasonable small tablet size.

Thus, it has been found that drug load of metformin HCl and compactability (compression force-crushing strength profile) of the tablets of this invention can be improved by surface treatment of metformin HCl with a water-soluble polymer, particularly copolyvidon.

Several water-soluble polymers including polyvinyl alcohol (PVA), hypromellose (HPMC), hydroxypropyl cellulose (HPC), methyl cellulose (MC), Povidone (PVP) and copolyvidon may be tested to improve compactability (compression force-crushing strength profile). As the results, PVA shows the best effect in terms of compactability but the manufacturability can be poor due to sticking problem during fluid-bed granulation. Further on, PVA may be not finally selected because of its negative impact on the stability of certain SGLT-2 inhibitors of this invention.

Formulation optimization studies have identified a composition with over 83% drug load of metformin HCl and improved crushing strength by surface-treatment of metformin HCl with the water-soluble polymer copolyvidon.

Therefore, finally, copolyvidon is selected and advantageously resulting in stable formulations and the viscosity of the granulating solution is enough low to prepare the aqueous solution and operate spraying by a fluid-bed granulator.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older.

As described hereinbefore by the administration of the pharmaceutical composition according to this invention and in particular in view of the high SGLT2 inhibitory activity of the SGLT2 inhibitors therein, excessive blood glucose is excreted through the urine of the patient, so that no gain in weight or even a reduction in body weight may result. Therefore, a treatment or prophylaxis according to this invention is advantageously suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. The pharmaceutical composition as well as the methods according to the present invention allow a reduction of the HbA1c value to a desired target range, for example <7% and preferably <6.5%, for a higher number of patients and for a longer time of therapeutic treatment compared with a corresponding monotherapy or a therapy using only two of the combination partners.

The pharmaceutical composition according to this invention and in particular the SGLT2 inhibitor therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 2.0%.

Furthermore, the method and/or use according to this invention is advantageously applicable in those patients who show one, two or more of the following conditions:

(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition for improving glycemic control in patients having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that an SGLT2 inhibitor as defined hereinbefore and hereinafter is administered to the patient.

According to another preferred embodiment of the present invention, there is provided a method for improving glycemic control in patients, in particular in adult patients, with type 2 diabetes mellitus as an adjunct to diet and exercise.

Therefore, the method and/or use according to this invention is advantageously applicable in those patients who show one, two or more of the following conditions:
(a) insufficient glycemic control with diet and exercise alone;
(b) insufficient glycemic control despite oral monotherapy with metformin, in particular despite oral monotherapy at a maximal tolerated dose of metformin;
(c) insufficient glycemic control despite oral monotherapy with another antidiabetic agent, in particular despite oral monotherapy at a maximal tolerated dose of the other antidiabetic agent.

The lowering of the blood glucose level by the administration of an SGLT2 inhibitor according to this invention is insulin-independent. Therefore, a pharmaceutical composition according to this invention is particularly suitable in the treatment of patients who are diagnosed having one or more of the following conditions
 insulin resistance,
 hyperinsulinemia,
 pre-diabetes,
 type 2 diabetes mellitus, particular having a late stage type 2 diabetes mellitus,
 type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

A pharmaceutical composition according to this invention exhibits a good safety profile. Therefore, a treatment or prophylaxis according to this invention is advantageously possible in those patients for which the mono-therapy with another antidiabetic drug, such as for example metformin, is contraindicated and/or who have an intolerance against such drugs at therapeutic doses. In particular, a treatment or prophylaxis according to this invention may be advantageously possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the SGLT2 inhibitor and partner drug according to this invention is included in the pharmaceutical composition or dosage form in an amount sufficient that by its administration the glycemic control in the patient to be treated is improved.

In the following preferred ranges of the amount of the SGLT2 inhibitor and partner drug to be employed in the pharmaceutical composition and the methods and uses according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient.

Within the scope of the present invention, the pharmaceutical composition is preferably administered orally. Other forms of administration are possible and described hereinafter. Preferably the one or more dosage forms comprising the SGLT2 inhibitor and partner drug are oral or usually well known.

A pharmaceutical composition which is present as a separate or multiple dosage form, preferably as a kit of parts, is useful in combination therapy to flexibly suit the individual therapeutic needs of the patient.

According to a first embodiment a preferred kit of parts comprises a containment containing a dosage form comprising the SGLT2 inhibitor and partner drug and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

According to a first embodiment a manufacture comprises (a) a pharmaceutical composition according to the present invention and (b) a label or package insert which comprises instructions that the medicament is to be administered.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, subcutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers which must be "acceptable" in the sense of being compatible with the other ingredients of the formulation and not deleterious to the recipient thereof. Examples of pharmaceutically acceptable carriers are known to the one skilled in the art.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore. Advantageous effects may be seen for example with respect to efficacy, dosage strength, dosage frequency, pharmacodynamic properties, pharmacokinetic properties, fewer adverse effects, convenience, compliance, etc.

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture are described in the WO 2006/120208 and WO 2007/031548. With regard to compound (I.9) an advantageous crystalline form is described in the international patent application WO 2006/117359 which hereby is incorporated herein in its entirety.

The active ingredients may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The active ingredients or a pharmaceutically acceptable salt thereof may be present in the form of a solvate such as a hydrate or alcohol adduct.

Any of the above mentioned pharmaceutical compositions and methods within the scope of the invention may be tested by animal models known in the art. In the following, in vivo experiments are described which are suitable to evaluate pharmacologically relevant properties of pharmaceutical compositions and methods according to this invention.

Pharmaceutical compositions and methods according to this invention can be tested in genetically hyperinsulinemic or diabetic animals like db/db mice, ob/ob mice, Zucker Fatty (fa/fa) rats or Zucker Diabetic Fatty (ZDF) rats. In addition, they can be tested in animals with experimentally induced diabetes like HanWistar or Sprague Dawley rats pretreated with streptozotocin.

The effect on glycemic control according to this invention can be tested after single dosing in an oral glucose tolerance test in the animal models described hereinbefore. The time course of blood glucose is followed after an oral glucose challenge in overnight fasted animals. The pharmaceutical compositions according to the present invention significantly improve glucose excursion, for example compared to another monotherapy, as measured by reduction of peak glucose concentrations or reduction of glucose AUC. In addition, after multiple dosing in the animal models described hereinbefore, the effect on glycemic control can be determined by measuring the HbA1c value in blood. The pharmaceutical compositions according to this invention significantly reduce HbA1c, for example compared to another monotherapy or compared to a dual-combination therapy.

The improved independence from insulin of the treatment according to this invention can be shown after single dosing in oral glucose tolerance tests in the animal models described hereinbefore. The time course of plasma insulin is followed after a glucose challenge in overnight fasted animals.

The increase in active GLP-1 levels by treatment according to this invention after single or multiple dosing can be determined by measuring those levels in the plasma of animal models described hereinbefore in either the fasting or postprandial state. Likewise, a reduction in glucagon levels in plasma can be measured under the same conditions.

The effect of a SGLT2 inhibitor and partner drug according to the present invention on beta-cell regeneration and neogenesis can be determined after multiple dosing in the animal models described hereinbefore by measuring the increase in pancreatic insulin content, or by measuring increased beta-cell mass by morphometric analysis after immunohistochemical staining of pancreatic sections, or by measuring increased glucose-stimulated insulin secretion in isolated pancreatic islets.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

1. Mono-Layer Tablet

Examples of the composition of mono-layer tablets for a SGLT-2 inhibitor of this invention (compound (I.9), or a crystalline form (I.9X) of compound (I.9))+metformin HCl FDC (Film-coated Tablets) is shown in Tables 1.1 to 1.11.

TABLE 1.1

Examples of composition of SGLT-2 inhibitor + Metformin HCl FDC Mono-layer Tablets

| | Dose Strength (SGLT-2 inhibitor/metformin HCl), mg | | | | | |
|---|---|---|---|---|---|---|
| | 12.5/500 | | 12.5/850 | | 12.5/1000 | |
| Ingredient | [mg] | [%] | [mg] | [%] | [mg] | [%] |
| Compound (I.9), or crystalline form (I.9X) of compound (I.9) | 12.50 | 2.11 | 12.50 | 1.25 | 12.50 | 1.06 |
| Metformin Hydrochloride | 500.0 | 84.76 | 850.0 | 85.0 | 1000.0 | 84.75 |
| Corn starch | 22.63 | 3.83 | 44.5 | 4.45 | 57.7 | 4.89 |
| Copovidone | 47.2 | 8.0 | 80.0 | 8.0 | 94.4 | 8.0 |
| Colloidal Anhydrous Silica | 2.95 | 0.5 | 5.0 | 0.5 | 5.9 | 0.5 |
| Magnesium stearate | 4.72 | 0.8 | 8.0 | 0.8 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.76 | 23.00 | 3.68 | 24.00 | 4.14 | 24.00 |
| Iron oxide, black | 0.12 | 1.00 | 0.16 | 1.00 | 0.18 | 1.00 |
| Iron oxide, red | 0.12 | 1.00 | 0.16 | 1.00 | 0.18 | 1.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.2

Examples of composition of SGLT-2 inhibitor + Metformin HCl FDC Mono-layer Tablets

| Ingredient | Dose Strength (SGLT-2 inhibitor/metformin HCl), mg | | | | | |
|---|---|---|---|---|---|---|
| | 12.5/500 | | 12.5/850 | | 12.5/1000 | |
| | [mg] | [%] | [mg] | [%] | [mg] | [%] |
| Compound (I.9), or crystalline form (I.9X) of compound (I.9) | 12.50 | 2.12 | 12.50 | 1.25 | 12.50 | 1.06 |
| Metformin Hydrochloride | 500.0 | 84.75 | 850.0 | 85.0 | 1000.0 | 84.75 |
| Corn starch | 22.63 | 3.83 | 44.5 | 4.45 | 57.76 | 4.89 |
| Copovidone | 47.2 | 8.0 | 80.0 | 8.0 | 94.4 | 8.0 |
| Colloidal Anhydrous Silica | 2.95 | 0.5 | 5.0 | 0.5 | 5.9 | 0.5 |
| Magnesium stearate | 4.72 | 0.8 | 8.0 | 0.8 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Macrogol 400 | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.928 | 24.40 | 3.744 | 23.40 | 3.78 | 21.00 |
| Iron oxide, black | 0.036 | 0.30 | 0.128 | 0.80 | 0.36 | 2.00 |
| Iron oxide, red | 0.036 | 0.30 | 0.128 | 0.80 | 0.36 | 2.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.3

Examples of composition of SGLT-2 inhibitor + Metformin HCl FDC Mono-layer Tablets

| Ingredient | Dose Strength (SGLT-2 inhibitor/metformin HCl), mg | | | | | |
|---|---|---|---|---|---|---|
| | 5/500 | | 5/850 | | 5/1000 | |
| | [mg] | [%] | [mg] | [%] | [mg] | [%] |
| Compound (I.9), or crystalline form (I.9X) of compound (I.9) | 5.00 | 0.85 | 5.00 | 0.50 | 5.00 | 0.42 |
| Metformin Hydrochloride | 500.0 | 84.76 | 850.00 | 85.00 | 1000.00 | 84.75 |
| Corn starch | 30.13 | 5.09 | 52.00 | 5.20 | 65.26 | 5.53 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.76 | 23.00 | 3.68 | 24.00 | 4.14 | 24.00 |
| Iron oxide, black | 0.12 | 1.00 | 0.16 | 1.00 | 0.18 | 1.00 |
| Iron oxide, red | 0.12 | 1.00 | 0.16 | 1.00 | 0.18 | 1.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.4

Examples of composition of SGLT-2 inhibitor + Metformin HCl FDC Mono-layer Tablets

| Ingredient | Dose Strength (SGLT-2 inhibitor/metformin HCl), mg | | | | | |
|---|---|---|---|---|---|---|
| | 5/500 | | 5/850 | | 5/1000 | |
| | [mg] | [%] | [mg] | [%] | [mg] | [%] |
| Compound (I.9), or crystalline form (I.9X) of compound (I.9) | 5.00 | 0.85 | 5.00 | 0.50 | 5.00 | 0.42 |
| Metformin Hydrochloride | 500.0 | 84.75 | 850.00 | 85.00 | 1000.00 | 84.75 |
| Corn starch | 30.13 | 5.10 | 52.00 | 5.20 | 65.26 | 5.53 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Macrogol 400 | 0.60 | 5.00 | 0.80 | 5.00 | 0.90 | 5.00 |

TABLE 1.4-continued

Examples of composition of SGLT-2 inhibitor + Metformin HCl FDC Mono-layer Tablets

| Ingredient | Dose Strength (SGLT-2 inhibitor/metformin HCl), mg | | | | | |
|---|---|---|---|---|---|---|
| | 5/500 | | 5/850 | | 5/1000 | |
| | [mg] | [%] | [mg] | [%] | [mg] | [%] |
| Talc | 2.40 | 20.00 | 3.20 | 20.00 | 3.60 | 20.00 |
| Titanium dioxide | 2.928 | 24.40 | 3.744 | 23.40 | 3.78 | 21.00 |
| Iron oxide, black | 0.036 | 0.30 | 0.128 | 0.80 | 0.36 | 2.00 |
| Iron oxide, red | 0.036 | 0.30 | 0.128 | 0.80 | 0.36 | 2.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.5

Examples of composition of SGLT-2 inhibitor + Metformin HCl FDC Mono-layer Tablets

| Ingredient | Dose Strength (SGLT-2 inhibitor/metformin HCl), mg | | | | | |
|---|---|---|---|---|---|---|
| | 12.5/500 | | 12.5/850 | | 12.5/1000 | |
| | [mg] | [%] | [mg] | [%] | [mg] | [%] |
| Compound (I.9), or crystalline form (I.9X) of compound (I.9) | 12.50 | 2.12 | 12.50 | 1.25 | 12.50 | 1.06 |
| Metformin Hydrochloride | 500.0 | 84.75 | 850.0 | 85.0 | 1000.0 | 84.75 |
| Corn starch | 22.63 | 3.83 | 44.5 | 4.45 | 57.76 | 4.89 |
| Copovidone | 47.2 | 8.0 | 80.0 | 8.0 | 94.4 | 8.0 |
| Colloidal Anhydrous Silica | 2.95 | 0.5 | 5.0 | 0.5 | 5.9 | 0.5 |
| Magnesium stearate | 4.72 | 0.8 | 8.0 | 0.8 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Macrogol 400 | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.928 | 24.40 | 3.744 | 23.40 | 3.78 | 21.00 |
| Iron oxide, black | 0.0012 | 0.10 | 0.08 | 0.50 | 0.36 | 2.00 |
| Iron oxide, red | 0.0012 | 0.10 | 0.08 | 0.50 | 0.36 | 2.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.6

Examples of composition of SGLT-2 inhibitor + Metformin HCl FDC Mono-layer Tablets

| Ingredient | Dose Strength (SGLT-2 inhibitor/metformin HCl), mg | | | | | |
|---|---|---|---|---|---|---|
| | 5/500 | | 5/850 | | 5/1000 | |
| | [mg] | [%] | [mg] | [%] | [mg] | [%] |
| Compound (I.9), or crystalline form (I.9X) of compound (I.9) | 5.00 | 0.85 | 5.00 | 0.50 | 5.00 | 0.42 |
| Metformin Hydrochloride | 500.0 | 84.75 | 850.00 | 85.00 | 1000.00 | 84.75 |
| Corn starch | 30.13 | 5.10 | 52.00 | 5.20 | 65.26 | 5.53 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Macrogol 400 | 0.60 | 5.00 | 0.80 | 5.00 | 0.90 | 5.00 |

TABLE 1.6-continued

Examples of composition of SGLT-2 inhibitor + Metformin HCl FDC Mono-layer Tablets

| | Dose Strength (SGLT-2 inhibitor/metformin HCl), mg | | | | | |
|---|---|---|---|---|---|---|
| | 5/500 | | 5/850 | | 5/1000 | |
| Ingredient | [mg] | [%] | [mg] | [%] | [mg] | [%] |
| Talc | 2.40 | 20.00 | 3.20 | 20.00 | 3.60 | 20.00 |
| Titanium dioxide | 2.928 | 24.40 | 3.744 | 23.40 | 3.78 | 21.00 |
| Iron oxide, black | 0.0012 | 0.10 | 0.08 | 0.50 | 0.36 | 2.00 |
| Iron oxide, red | 0.0012 | 0.10 | 0.08 | 0.50 | 0.36 | 2.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.7

Examples of the composition of SGLT-2 inhibitor + Metformin HCl FDC Mono-layer Tablets

| | Dose Strength (SGLT-2 inhibitor/metformin HCl), mg | | | | | |
|---|---|---|---|---|---|---|
| | 1.25/500 | | 1.25/850 | | 1.25/1000 | |
| Ingredient | [mg] | [%] | [mg] | [%] | [mg] | [%] |
| Compound (I.9), or crystalline form (I.9X) of compound (I.9) | 1.25 | 0.21 | 1.25 | 0.125 | 1.25 | 0.10 |
| Metformin Hydrochloride | 500.0 | 84.76 | 850.00 | 85.00 | 1000.00 | 84.75 |
| Corn starch | 33.88 | 5.73 | 55.75 | 5.575 | 69.01 | 5.85 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.76 | 23.00 | 3.68 | 24.00 | 4.14 | 24.00 |
| Iron oxide, black | 0.12 | 1.00 | 0.16 | 1.00 | 0.18 | 1.00 |
| Iron oxide, red | 0.12 | 1.00 | 0.16 | 1.00 | 0.18 | 1.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.8

Examples of the composition of SGLT-2 inhibitor + Metformin HCl FDC Mono-layer Tablets

| | Dose Strength (SGLT-2 inhibitor/metformin HCl), mg | | | | | |
|---|---|---|---|---|---|---|
| | 1.25/500 | | 1.25/850 | | 1.25/1000 | |
| Ingredient | [mg] | [%] | [mg] | [%] | [mg] | [%] |
| Compound (I.9), or crystalline form (I.9X) of compound (I.9) | 1.25 | 0.21 | 1.25 | 0.125 | 1.25 | 0.10 |
| Metformin Hydrochloride | 500.0 | 84.76 | 850.00 | 85.00 | 1000.00 | 84.75 |
| Corn starch | 33.88 | 5.73 | 55.75 | 5.575 | 69.01 | 5.85 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.52 | 21.00 | 3.36 | 21.00 | 3.78 | 21.00 |
| Iron oxide, black | 0.24 | 2.00 | 0.32 | 2.00 | 0.36 | 2.00 |
| Iron oxide, red | 0.24 | 2.00 | 0.32 | 2.00 | 0.36 | 2.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.9

Examples of the composition of SGLT-2 inhibitor + Metformin HCl FDC Mono-layer Tablets with MCC

| | Dose Strength (SGLT-2 inhibitor/metformin HCl), mg | | | | | |
|---|---|---|---|---|---|---|
| | 1.25/500 | | 1.25/850 | | 1.25/1000 | |
| Ingredient | [mg] | [%] | [mg] | [%] | [mg] | [%] |
| Compound (I.9), or crystalline form (I.9X) of compound (I.9) | 1.25 | 0.21 | 1.25 | 0.125 | 1.25 | 0.10 |
| Metformin Hydrochloride | 500.0 | 84.76 | 850.00 | 85.00 | 1000.00 | 84.75 |
| Micro-crystalline cellulose | 33.88 | 5.73 | 55.75 | 5.575 | 69.01 | 5.85 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.76 | 23.00 | 3.68 | 23.00 | 4.14 | 23.00 |
| Iron oxide, black | 0.12 | 1.00 | 0.16 | 1.00 | 0.18 | 1.00 |
| Iron oxide, red | 0.12 | 1.00 | 0.16 | 1.00 | 0.18 | 1.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.10

Examples of the composition of SGLT-2 inhibitor + Metformin HCl FDC Mono-layer Tablets with MCC

| | Dose Strength (SGLT-2 inhibitor/metformin HCl), mg | | | | | |
|---|---|---|---|---|---|---|
| | 12.5/500 | | 12.5/850 | | 12.5/1000 | |
| Ingredient | [mg] | [%] | [mg] | [%] | [mg] | [%] |
| Compound (I.9), or crystalline form (I.9X) of compound (I.9) | 12.50 | 2.11 | 12.50 | 1.25 | 12.50 | 1.06 |
| Metformin Hydrochloride | 500.0 | 84.76 | 850.00 | 85.00 | 1000.00 | 84.75 |
| Micro-crystalline cellulose | 22.63 | 3.83 | 44.50 | 4.45 | 57.70 | 4.89 |
| Copovidone | 47.20 | 8.00 | 80.00 | 8.00 | 94.40 | 8.00 |
| Colloidal Anhydrous Silica | 2.95 | 0.50 | 5.00 | 0.50 | 5.90 | 0.50 |
| Magnesium stearate | 4.72 | 0.80 | 8.00 | 0.80 | 9.44 | 0.80 |
| Total Mass (tablet core) | 590.00 | 100.00 | 1000.00 | 100.00 | 1180.00 | 100.00 |
| Hypromellose 2910 | 6.00 | 50.00 | 8.00 | 50.00 | 9.00 | 50.00 |
| Propylene glycol | 0.60 | 5.00 | 0.80 | 5.00 | 0.90 | 5.00 |
| Talc | 2.40 | 20.00 | 3.20 | 20.00 | 3.60 | 20.00 |
| Titanium dioxide | 2.76 | 23.00 | 3.68 | 23.00 | 4.14 | 23.00 |
| Iron oxide, black | 0.12 | 1.00 | 0.16 | 1.00 | 0.18 | 1.00 |
| Iron oxide, red | 0.12 | 1.00 | 0.16 | 1.00 | 0.18 | 1.00 |
| Total Mass (film-coat) | 12.00 | 100.00 | 16.00 | 100.00 | 18.00 | 100.00 |
| Total Mass (coated tablet) | 602.00 | | 1016.00 | | 1198.00 | |

TABLE 1.11

Examples of composition of SGLT-2 inhibitor + Metformin HCl FDC Mono-layer Tablets

| | Dose Strength (SGLT-2 inhibitor/metformin HCl), mg | | |
|---|---|---|---|
| Material | mg/tablet (Sum) | | |
| Compound (I.9), or crystalline form (I.9X) of compound (I.9) | 5.000 mg | 5.000 mg | 5.000 mg |
| Metformin HCl, milled | 500.000 mg | 850.000 mg | 1000.000 mg |
| Corn starch, undried | 30.130 mg | 54.721 mg | 65.260 mg |
| Copovidone | 47.200 mg | 80.240 mg | 94.400 mg |
| Water, purified * | 175.000 mg | 297.500 mg | 350.000 mg |
| Colloidal Anhydrous Silica | 2.950 mg | 5.015 mg | 5.900 mg |
| Magnesium stearate | 4.720 mg | 8.024 mg | 9.440 mg |
| Total (core) | 590.000 mg | 1003.000 mg | 1180.000 mg |
| Hypromellose 2910 | 6.000 mg | 8.500 mg | 9.500 mg |
| Macrogol 400 | 0.600 mg | 0.850 mg | 0.950 mg |
| Titanium dioxide | 2.880 mg | 4.216 mg | 3.990 mg |
| Talc | 2.400 mg | 3.400 mg | 3.800 mg |

TABLE 1.11-continued

Examples of composition of SGLT-2 inhibitor + Metformin HCl FDC Mono-layer Tablets

| | | | |
|---|---|---|---|
| Iron oxide, black | 0.060 mg | 0.017 mg | 0.380 mg |
| Iron oxide, red | 0.060 mg | 0.017 mg | 0.380 mg |
| Water, purified * | 84.000 mg | 119.000 mg | 133.000 mg |
| | | | |
| Total (film coated tablet) | 602.000 mg | 1020.000 mg | 1199.000 mg |
| Name of colours: (or shift of colours between dose strengths) | pale grayish brown to pale grayish ruby | pinkish white | dark grayish brown to dark grayish ruby |

Dose Strength (SGLT-2 inhibitor/metformin HCl), mg

| Material | mg/tablet (Sum) | | |
|---|---|---|---|
| Compound (I.9), or crystalline form (I.9X) of compound (I.9) | 12.500 mg | 12.500 mg | 12.500 mg |
| Metformin HCl, milled | 500.000 mg | 850.000 mg | 1000.000 mg |
| Corn starch, undried | 22.630 mg | 47.221 mg | 57.760 mg |
| Copovidone | 47.200 mg | 80.240 mg | 94.400 mg |
| Water, purified * | 175.000 mg | 297.500 mg | 350.000 mg |
| Colloidal Anhydrous Silica | 2.950 mg | 5.015 mg | 5.900 mg |
| Magnesium stearate | 4.720 mg | 8.024 mg | 9.440 mg |
| | | | |
| Total (core) | 590.000 mg | 1003.000 mg | 1180.000 mg |
| Hypromellose 2910 | 6.000 mg | 8.500 mg | 9.500 mg |
| Macrogol 400 | 0.600 mg | 0.850 mg | 0.950 mg |
| Titanium dioxide | 2.880 mg | 4.216 mg | 3.990 mg |
| Talc | 2.400 mg | 3.400 mg | 3.800 mg |
| Iron oxide, black | 0.060 mg | 0.017 mg | 0.380 mg |
| Iron oxide, red | 0.060 mg | 0.017 mg | 0.380 mg |
| Water, purified * | 84.000 mg | 119.000mg | 133.000 mg |
| | | | |
| Total (film coated tablet) | 602.000 mg | 1020.000 mg | 1199.000 mg |
| Name of colours: (or shift of colours between dose strengths) | pale grayish brown to pale grayish ruby | pinkish white | dark grayish brown to dark grayish ruby |

Dose Strength (SGLT-2 inhibitor/metformin HCl), mg

| Material | 5/500 | 5/850 | 5/1000 |
|---|---|---|---|
| Compound (I.9), or crystalline form (I.9X) of compound (I.9) | 0.85% | 0.50% | 0.42% |
| Metformin HCl, milled | 84.75% | 84.75% | 84.75% |
| Corn starch, undried | 5.11% | 5.46% | 5.53% |
| Copovidone | 8.00% | 8.00% | 8.00% |
| Water, purified * | | | |
| Colloidal Anhydrous Silica | 0.50% | 0.50% | 0.50% |
| Magnesium stearate | 0.80% | 0.80% | 0.80% |
| | | | |
| Total (core) | 100.00% | 100.00% | 100.00% |
| Hypromellose 2910 | 50.00% | 50.00% | 50.00% |
| Macrogol 400 | 5.00% | 5.00% | 5.00% |
| Titanium dioxide | 24.00% | 24.80% | 21.00% |
| Talc | 20.00% | 20.00% | 20.00% |
| Iron oxide, black | 0.50% | 0.10% | 2.00% |
| Iron oxide, red | 0.50% | 0.10% | 2.00% |
| Water, purified * | | | |
| Total (film coated tablet) | 100.00% | 100.00% | 100.00% |

Dose Strength (SGLT-2 inhibitor/metformin HCl), mg

| Material | 12.5/500 | 12.5/850 | 12.5/1000 |
|---|---|---|---|
| Compound (I.9), or crystalline form (I.9X) of compound (I.9) | 2.12% | 1.25% | 1.06% |
| Metformin HCl, milled | 84.75% | 84.75% | 84.75% |
| Corn starch, undried | 3.84% | 4.71% | 4.89% |
| Copovidone | 8.00% | 8.00% | 8.00% |
| Water, purified * | | | |
| Colloidal Anhydrous Silica | 0.50% | 0.50% | 0.50% |
| Magnesium stearate | 0.80% | 0.80% | 0.80% |
| | | | |
| Total (core) | 100.00% | 100.00% | 100.00% |
| Hypromellose 2910 | 50.00% | 50.00% | 50.00% |
| Macrogol 400 | 5.00% | 5.00% | 5.00% |

TABLE 1.11-continued

| Examples of composition of SGLT-2 inhibitor + Metformin HCl FDC Mono-layer Tablets | | | |
|---|---|---|---|
| Titanium dioxide | 24.00% | 24.80% | 21.00% |
| Talc | 20.00% | 20.00% | 20.00% |
| Iron oxide, black | 0.50% | 0.10% | 2.00% |
| Iron oxide, red | 0.50% | 0.10% | 2.00% |
| Water, purified * | | | |
| Total (film coated tablet) | 100.00% | 100.00% | 100.00% |

* Removed during processing, does not appear in the final product.

A broad dose range of SGLT-2 inhibitor, e.g. 1.25, 5 or 12.5 mg, could be used, in which case the amount of binder corn starch or microcrystalline cellulose is adjusted. Instead of corn starch, microcrystalline cellulose could be used. In the further description of the manufacturing procedure only corn starch is described.

Manufacturing Procedure (Mono-Layer Tablets):

SGLT-2 inhibitor of this invention (e.g. compound (I.9), or crystalline form (I.9X) of compound (I.9))+metformin HCl FDC mono-layer tablets are produced by a fluid-bed granulation process and a conventional tableting process with a rotary press. Metformin HCl and corn starch, the SGLT-2 inhibitor is either added as powder and premixed before fluid-bed granulation is conducted by spraying of "Granulation Liquid" composed of copolyvidon (Kollidon VA64 and purified water, or directly dispersed in the "granulation liquid". Alternatively, the SGLT-2 inhibitor is added as powder together with metformin-HCl and corn starch to the fluid bed granulator. After finishing of fluid-bed granulation, the granulate is sieved with a suitable screen. The sieved granulate is blended with colloidal anhydrous silica (Aerosil 200) and magnesium stearate as a lubricant. The final mixture is compressed into tablets using a conventional rotary tablet press.

The tablet cores may be film-coated by an aqueous film-coating suspension, containing hypromellose as film-forming agent, propylene glycol as plasticizer, talc as glidant and the pigments black, red, yellow iron oxide and mixture of red/yellow/black and titanium dioxide.

Narrative more specific description of the preferred manufacturing process for the mono-layer tablets:

a) Metformin HCl and corn starch are sieved using a screen with a mesh size of 0.5 to 1 mm before dispensing.
b) Compound (I.9), or crystalline form (I.9X) of compound (I.9)) and finally copolyvidon are dissolved resp. dispersed in purified water at ambient temperature with a propeller mixer to produce the "Granulation Liquid".
c) Metformin HCl and corn starch are sucked into a chamber of a suitable fluid-bed granulator and preheated up to a product temperature target of approx. 36° C. Preheating is optionally. Alternatively, the compound (I.9), or crystalline form (I.9X) of compound (I.9)) and metformin-HCl and corn starch are sucked into a chamber of suitable fluid-bed granulator.
d) Immediately after the product temperature target is reached, the "Granulation Liquid" is sprayed into the mixture for fluid-bed granulating under dry condition to avoid blocking during granulation.
e) At the end of spraying, the resultant granulate is dried at approx. 70 C inlet air temperature until the desired LOD value (i.e. 1-3%, for example 0.8-2%) is reached.
f) The granulate is sieved using a screen with a mesh size of 0.5 to 1.0 mm.
g) The sieved granulate and colloidal anhydrous silica (Aerosil 200) are blended with a suitable blender. Aerosil 200 should be pre-sieved with a small portion of the sieved granulate through a 0.8 mm-screen before use.
h) Magnesium stearate is passed through a 0.8 mm sieve and added into the granulate. Subsequently the "Final Blend" is produced by final blending in the free-fall blender.
i) The "Final Blend" is compressed into tablets with a rotary press.
j) Titanium dioxide, polyethylene glycol or propylene glycol and iron oxide (yellow, red, black or mixture thereof) are dispersed in purified water with a high shear homo-mixer. Then, hypromellose and talc are added and dispersed with a homo-mixer and propeller mixer at ambient temperature to produce the "Coating Suspension".
k) The tablet cores are coated with the "Coating Suspension" to the target weight gain to produce the "Film-coated Tablets". The "Coating Suspension" should be stirred again before use and kept stirring slowly during the coating (spraying) process.

Narrative more specific description of an alternative manufacturing process for the mono-layer tablets:

a) Metformin HCl is sieved using a screen with a mesh size of 0.5 to 1 mm before weighing.
b) copolyvidon are dissolved in purified water at ambient temperature with a propeller mixer to produce the "Granulation Liquid"
c) is added into the container, then blended with metformin HCl and corn starch in the fluid-bed granulator.
d) The "Granulation Liquid" is sprayed into the mixture for fluid-bed granulating under dry condition to avoid blocking during granulation.
e) At the end of spraying, the resultant granulate is dried at 70-80° C. until the desired LOD value (i.e. 1-3%, for example 0.8-2%), in case the LOD is more than 2%.
f) The granulate is sieved using a screen with a mesh size of 0.5 to 1.0 mm.
g) The sieved granulate and colloidal anhydrous silica (Aerosil 200) are blended with a suitable blender. Aerosil 200 should be sieved with a 0.5 mm-screen before use.
h) Magnesium stearate passed through a 0.5 mm sieve and added into the granulate. Subsequently the "Final Blend" is produced by final blending in the blender.
i) The "Final Blend" is compressed into tablets with a rotary press.
j) Hypromellose and polyethylene glycol or propylene glycol are dissolved in purified water with a propeller mixer. Talc, titanium dioxide, and iron oxide (yellow, red and/or black and mixture thereof) are dispersed in purified water with a homo-mixer. The suspension is added into the hypromellose solution, then mixed with a propeller mixer at ambient temperature to produce the "Coating Suspension".
k) The tablet cores are coated with the "Coating Suspension" to the target weight gain to produce the "Film-coated Tablets". The "Coating Suspension" should be stirred again before use and kept stirring slowly during the coating (spraying) process.

2. Bi-Layer Tablet

Examples of the composition of bi-layer tablets for a SGLT-2 inhibitor of this invention (compound (I.9), or a crystalline form (I.9X) of compound (I.9))+metformin HCl FDC (Film-coated Tablets) is shown in Table 2.

TABLE 2

Examples of the composition of SGLT-2 inhibitor + Metformin HCl Bi-layer Tablets

| Ingredient | Dose Strength (SGLT-2 inhibitor/metformin HCl), mg | | | Dose Strength (SGLT-2 inhibitor/metformin HCl), mg | | |
|---|---|---|---|---|---|---|
| | 12.5/500 [mg] | 12.5/850 [mg] | 12.5/1000 [mg] | 5/500 [mg] | 5/850 [mg] | 5/1000 [mg] |
| SGLT-2 inhibitor-portion: | (300) | (300) | (400) | (325) | (325) | (425) |
| compound (I.9), or crystalline form (I.9X) of compound (I.9)) | 12.50 | 12.50 | 12.50 | 5.00 | 5.00 | 5.00 |
| Lactose monohydrate | 165.50 | 165.50 | 165.50 | 181.25 | 181.25 | 181.25 |
| Cellulose microcrystalline | 125.00 | 125.00 | 125.00 | 131.25 | 131.25 | 131.25 |
| Hydroxypropylcellulose | 3.00 | 3.00 | 3.00 | 3.75 | 3.75 | 3.75 |
| Croscarmellose sodium | 2.00 | 2.00 | 2.00 | 2.50 | 2.50 | 2.50 |
| Colloidal silicium dioxide | 0.50 | 0.50 | 0.50 | 0.025 | 0.625 | 0.625 |
| Magnesium stearate | 0.50 | 0.50 | 0.50 | 0.625 | 0.625 | 0.625 |
| Metformin HCl-portion: | (570) | (969) | (1140) | (570) | (969) | (1140) |
| Metformin Hydrochloride | 500.0 | 850.00 | 1000.00 | 500.0 | 850.00 | 1000.00 |
| Corn starch | 15.00 | 25.50 | 30.00 | 15.00 | 25.50 | 30.00 |
| Copovidone | 47.50 | 80.57 | 95.00 | 47.50 | 80.57 | 95.00 |
| Colloidal Anhydrous Silica | 2.50 | 4.25 | 5.00 | 2.50 | 4.25 | 5.00 |
| Magnesium stearate | 5.00 | 8.50 | 10.00 | 5.00 | 8.50 | 10.00 |
| Total Mass (tablet core) | 870.0 | 1269.0 | 1540.0 | 895.0 | 1494.0 | 1565.0 |
| Hypromellose 2910 | 7.00 | 9.00 | 10.00 | 7.00 | 9.00 | 10.00 |
| Propylene glycol | 0.70 | 0.90 | 1.00 | 0.70 | 0.90 | 1.00 |
| Talc | 2.80 | 3.60 | 4.00 | 2.80 | 3.60 | 4.00 |
| Titanium dioxide | 3.22 | 4.14 | 4.60 | 3.22 | 4.14 | 4.60 |
| Iron oxide, black | 0.14 | 0.18 | 0.20 | 0.14 | 0.18 | 0.20 |
| Iron oxide, red | 0.14 | 0.18 | 0.20 | 0.14 | 0.18 | 0.20 |
| Total Mass (film-coat) | 14.00 | 18.000 | 20.000 | 14.00 | 18.000 | 20.000 |
| Total Mass (coated tablet) | 684.00 | 1087.00 | 1260.00 | 709.00 | 1112.00 | 1285.00 |

A broad dose range of SGLT-2 inhibitor, eg. 1.25, 5 or 12.5 mg, could be used, in which case the amount of binder corn starch or microcrystalline cellulose is adjusted. Instead of corn starch, microcrystalline cellulose could be used. In the further description of the manufacturing procedure only corn starch is described.

Manufacturing Procedure (Bi-Layer Tablets):

SGLT-2 inhibitor of this invention (e.g. compound (I.9), or crystalline form (I.9X) of compound (I.9))+metformin HCl FDC bi-layer tablets are produced by a high-shear wet granulation process (for SGLT-2 inhibitor-granulate), a fluid-bed granulation process (for metformin HCl-granulate), and bi-layer tableting process with a multi-layer rotary press.

SGLT-2 inhibitor-granulate: By using a high-shear granulator the active SGLT-2 inhibitor. The overall manufacturing process consisted of following steps:
1) Screen hydroxypropyl cellulose (HPC)
2) Add the intra-granular microcrystalline cellulose portion. SGLT-2 inhibitor, lactose, HPC and croscarmellose sodium to the granulator
3) Granulate the blend with water.
4) Dry the granulate in Fluid bed drier: less than 1.5% LOD
5) Mill the granulation into the blender container
   Quadro mill
   Quadro mill screen—18 mesh.
6) Screen the following onto milled granulation in the container of a tumble blender
   Premix of the colloidal silicon dioxide with a portion of the extra-granular microcrystalline cellulose screened through 20-25 mesh.
   Remainder of the extra-granular microcrystalline cellulose and blend.
7) Premix the magnesium stearate with a portion of the blended granulation, screen (18 mesh) onto the remainder of the granulation in the blender.

Subsequently the "Final Blend A" is produced by final blending in a suitable blender.

Metformin HCl-granulate: Metformin HCl and corn starch, fluid-bed granulation is conducted by spraying of "Granulation Liquid" composed of copovidon (Kollidon VA64) and purified water. Alternatively, the SGLT-2 inhibitor is added as powder together with metformin-HCl and corn starch to the fluid bed granulator. After finishing of fluid-bed granulation, the granulate is sieved with a suitable screen. The sieved granulate is blended with colloidal anhydrous silica (Aerosil 200) and magnesium stearate as a lubricant.

Narrative more specific description of the manufacturing process for the Metformin HCl-granulate:
a) Metformin HCl is sieved using a screen with a mesh size of 0.5 to 1 mm before weighing.

b) Copolyvidon is dissolved in purified water at ambient temperature with a propeller mixer to produce the "Granulation Liquid"
c) The "Granulation Liquid" is sprayed into the mixture for fluid-bed granulating under dry condition to avoid blocking during granulation.
d) At the end of spraying, the resultant granulate is dried at 70-80° C. until the desired LOD value (i.e. 0.8-2%, for example 1-2%), in case the LOD is more than 2%.
e) The granulate is sieved using a screen with a mesh size of 0.5 to 1.0 mm.
f) The sieved granulate and colloidal anhydrous silica (Aerosil 200) are blended with a suitable blender. Aerosil 200 should be sieved with a 0.5 mm-screen before use.
g) Magnesium stearate passed through a 0.5 mm sieve and added into the granulate.
Subsequently the "Final Blend B" is produced by final blending in the blender.

The "Final Blend A" and "Final Blend B" are compressed into bi-layer tablets using a multi-layer rotary press. The tablet cores may be film-coated by an aqueous film-coating suspension, containing hypromellose as film-forming agent, polyethylene glycol or propylene glycol as plasticizer, talc as glidant and the pigments yellow, red, black iron oxide and mixture thereof and titanium dioxide.

Narrative more specific description of the manufacturing process for the film-coating:
a) Hypromellose and polyethylene glycol or propylene glycol are dissolved in purified water with a propeller mixer. Talc, titanium dioxide, and iron oxide (yellow, red or yellow and red) are dispersed in purified water with a homo-mixer. The suspension is added into the hypromellose solution, then mixed with a propeller mixer at ambient temperature to produce the "Coating Suspension".
b) The tablet cores are coated with the "Coating Suspension" to the target weight gain to produce the "Film-coated Tablets". The "Coating Suspension" should be stirred again before use and kept stirring slowly during the coating (spraying) process.

3. Tablet-in-Tablet or Bull's Eye Tablet

Examples of the composition of Tablet-in-Tablet or Bull's eye tablets for a SGLT-2 inhibitor of this invention (compound (I.9), or crystalline form (I.9X) of compound (I.9))+ metformin HCl FDC (Film-coated Tablets) is shown in Table 3.

TABLE 3

Examples of the composition of compound (I.9), or crystalline form (I.9X) of compound (I.9)) + Metformin HCl FDC Tablet-in-Tablet or Bull's Eye Tablets

| Ingredient | Dose Strength (SGLT-2 inhibitor/metformin HCl), mg | | | Dose Strength (SGLT-2 inhibitor/metformin HCl), mg | | |
|---|---|---|---|---|---|---|
| | 12.5/500 [mg] | 12.5/850 [mg] | 12.5/1000 [mg] | 5/500 [mg] | 5/850 [mg] | 5/1000 [mg] |
| SGLT-2 inhibitor-portion: | (100) | (100) | (100) | (125) | (125) | (125) |
| compound (I.9), or crystalline form (I.9X) of compound (I.9)) | 12.50 | 12.50 | 12.50 | 5.00 | 5.00 | 5.00 |
| Lactose monohydrate | 65.50 | 65.50 | 65.50 | 81.25 | 81.25 | 81.25 |
| Cellulose microcrystalline | 25.00 | 25.00 | 25.00 | 31.25 | 31.25 | 31.25 |
| Hydroxypropylcellulose | 3.00 | 3.00 | 3.00 | 3.75 | 3.75 | 3.75 |
| Croscarmellose sodium | 2.00 | 2.00 | 2.00 | 2.50 | 2.50 | 2.50 |
| Colloidal silicium dioxide | 0.50 | 0.50 | 0.50 | 0.025 | 0.625 | 0.625 |
| Magnesium stearate | 0.50 | 0.50 | 0.50 | 0.625 | 0.625 | 0.625 |
| Metformin HCl-portion: | (570) | (969) | (1140) | (570) | (969) | (1140) |
| Metformin Hydrochloride | 500.0 | 850.00 | 1000.00 | 500.0 | 850.00 | 1000.00 |
| Corn starch | 15.00 | 25.50 | 30.00 | 15.00 | 25.50 | 30.00 |
| Copovidone | 47.50 | 80.57 | 95.00 | 47.50 | 80.57 | 95.00 |
| Colloidal Anhydrous Silica | 2.50 | 4.25 | 5.00 | 2.50 | 4.25 | 5.00 |
| Magnesium stearate | 5.00 | 8.50 | 10.00 | 5.00 | 8.50 | 10.00 |
| Total Mass (tablet core) | 670 | 1069 | 1240 | 695 | 1094.00 | 1265.00 |
| Hypromellose 2910 | 6.00 | 8.00 | 9.00 | 6.00 | 8.00 | 9.00 |
| Propylene glycol | 0.60 | 0.80 | 0.90 | 0.60 | 0.80 | 0.90 |
| Talc | 2.40 | 3.20 | 3.60 | 2.40 | 3.20 | 3.60 |
| Titanium dioxide | 2.76 | 3.68 | 4.14 | 2.76 | 3.68 | 4.14 |
| Iron oxide, black | 0.12 | 0.16 | 0.18 | 0.12 | 0.16 | 0.18 |
| Iron oxide, red | 0.12 | 0.16 | 0.18 | 0.12 | 0.16 | 0.18 |
| Total Mass (film-coat) | 12.00 | 16.000 | 18.000 | 12.00 | 16.000 | 18.000 |
| Total Mass (coated tablet) | 682.00 | 1085.00 | 1258.00 | 707.00 | 1110.00 | 1283.00 |

A broad dose range of SGLT-2 inhibitor, eg. 1.25, 5 or 12.5 mg, could be used, in which case the amount of binder corn starch or microcrystalline cellulose is adjusted. Instead of corn starch, microcrystalline cellulose could be used. In the further description of the manufacturing procedure only corn starch is described.
Manufacturing Procedure (Tablet-in-Tablet or Bull's Eye Tablet):
SGLT-2 inhibitor of this invention (e.g. compound (I.9), or crystalline form (I.9X) of compound (I.9))+metformin HCl FDC Tablet-in-Tablet or Bull's eye tablets are produced by a high-shear wet granulation process (for SGLT-2 inhibitor-granulate), a rotary press (for SGLT-2 inhibitor core-tablet), a fluid-bed granulation process (for metformin HCl-granulate), and press-coating process with a press-coater.

SGLT-2 inhibitor-granulate: By using a high-shear granulator the active SGLT-2 inhibitor.

The overall manufacturing process consisted of following steps:
1) Screen hydroxypropyl cellulose (HPC)
2) Add the intra-granular microcrystalline cellulose portion. SGLT-2 inhibitor, lactose, HPC and croscarmellose sodium to the granulator
3) Granulate the blend with water.
4) Dry the granulate in Fluid bed drier: less than 1.5% LOD
5) Mill the granulation into the blender container
   Quadro mill with screen—18 mesh.
6) Screen the following onto milled granulation in the container of a tumble blender
   Premix of the colloidal silicon dioxide with a portion of the extra-granular microcrystalline cellulose screened through 20-25 mesh.
   Remainder of the extra-granular microcrystalline cellulose and blend.
7) Premix the magnesium stearate with a portion of the blended granulation, screen (18 mesh) onto the remainder of the granulation in the blender.
   Subsequently the "Final Blend" is produced by final blending in the free-fall blender.
8.) The "Final Blend" of the SGLT-2 inhibitor is compressed into tablets with a rotary press.

Metformin HCl-granulate: Metformin HCl and corn starch, fluid-bed granulation is conducted by spraying of "Granulation Liquid" composed of copolyvidon (Kollidon VA64) and purified water. Alternatively, the SGLT-2 inhibitor is added as powder together with metformin-HCl and corn starch to the fluid bed granulator. After finishing of fluid-bed granulation, the granulate is sieved with a suitable screen. The sieved granulate is blended with colloidal anhydrous silica (Aerosil 200) and magnesium stearate as a lubricant.

Narrative more specific description of the manufacturing process for the Metformin HCl-granulate:
a) Metformin HCl is sieved using a screen with a mesh size of 0.5 to 1 mm before weighing.
b) Copolyvidon is dissolved in purified water at ambient temperature with a propeller mixer to produce the "Granulation Liquid"
d) The "Granulation Liquid" is sprayed into the mixture for fluid-bed granulating under dry condition to avoid blocking during granulation.
e) At the end of spraying, the resultant granulate is dried at 70-80° C. until the desired LOD value (i.e. 0.8-2%, for example 1-2%), in case the LOD is more than 2%.
f) The granulate is sieved using a screen with a mesh size of 0.5 to 1.0 mm.
g) The sieved granulate and colloidal anhydrous silica (Aerosil 200) are blended with a suitable blender. Aerosil 200 should be sieved with a 0.5 mm-screen before use.
h) Magnesium stearate passed through a 0.5 mm sieve and added into the granulate. Subsequently "Metformin HCl-granulate" (Final Blend) is produced by final blending in the blender.

The "SGLT-2 inhibitor core-tablets" and "Metformin HCl-granulate" are compressed into Tablet-in-Tablet or Bull's eye tablets using a press-coater. The difference between the Tablet-in-Tablet and Bull's eye tablet is the position of the core tablet.

Narrative more specific description of the manufacturing process for the Tablet-in-Tablet:
a) Fill a half of Metformin HCl-granulate in a die.
b) Place a compound (I.9), or crystalline form (I.9X) of compound (I.9)) core-tablet on the surface of Metformin HCl-granulate.
c) Cover the core-tablet with second half of Metformin HCl-granulate, then compressed into the tablet (Tablet-in-Tablet).

Narrative more specific description of the manufacturing process for the Bull's eye tablets:
a) Fill Metformin HCl-granulate in a die.
b) Place the compound (I.9), or crystalline form (I.9X) of compound (I.9)) core-tablet on the Metformin HCl-granulate in the die, then compressed into the tablet (Bull's eye tablet).

The tablets may be film-coated by an aqueous film-coating suspension, containing hypromellose as film-forming agent, polyethylene glycol or propylene glycol as plasticizer, talc as glidant and the pigments yellow, red, black iron oxide and mixture thereof and titanium dioxide.

Narrative more specific description of the manufacturing process for the film-coating:
a) Hypromellose and polyethylene glycol or propylene glycol are dissolved in purified water with a propeller mixer. Talc, titanium dioxide, and iron oxide (yellow, red, black or mixture thereof) are dispersed in purified water with a homo-mixer. The suspension is added into the hypromellose solution, then mixed with a propeller mixer at ambient temperature to produce the "Coating Suspension".
b) The tablet cores are coated with the "Coating Suspension" to the target weight gain to produce the "Film-coated Tablets". The "Coating Suspension" should be stirred again before use and kept stirring slowly during the coating (spraying) process.

4. SGLT-2 Inhibitor—Drug Layering on Metformin HCl Tablet (Film-Coating for Drug-Loading)

Examples of the composition of a SGLT-2 inhibitor of this invention (Compound (I.9), or crystalline form (I.9X) of compound (I.9))+metformin HCl FDC (Film-coated Tablets) which are prepared by drug loading by film-coating on the Metformin HCl Tablet is shown in Table 4.

TABLE 4

Examples of the composition of Compound (I.9), or crystalline form (I.9X) of compound (I.9)) + Metformin HCl FDC SGLT-2 inhibitor-Coating on Metformin HCl Tablet

| Ingredient | Dose Strength (SGLT-2 inhibitor/metformin HCl), mg | | |
| --- | --- | --- | --- |
| | 12.5/500 [mg] | 12.5/850 [mg] | 12.5/1000 [mg] |
| Metformin HCl-portion: | (570) | (969) | (1140) |
| Metformin Hydrochloride | 500.0 | 850.0 | 1000.0 |
| Corn starch | 15.0 | 25.5 | 30.0 |
| Copovidone | 47.5 | 80.57 | 95.0 |
| Colloidal Anhydrous Silica | 2.5 | 4.25 | 5.0 |
| Magnesium stearate | 5.0 | 8.5 | 10.0 |
| Total Mass (tablet core) | 570 | 969 | 1140 |
| Seal-coat (seal-coating): | (12) | (16) | (18) |
| Hypromellose 2910 | 6.00 | 8.00 | 9.00 |
| Propylene glycol | 0.60 | 0.80 | 0.90 |
| Talc | 2.22 | 2.96 | 3.33 |
| Titanium dioxide | 3.00 | 4.00 | 4.50 |

TABLE 4-continued

Examples of the composition of Compound (I.9), or crystalline form (I.9X) of compound (I.9)) + Metformin HCl FDC SGLT-2 inhibitor-Coating on Metformin HCl Tablet

| | Dose Strength (SGLT-2 inhibitor/metformin HCl), mg | | |
|---|---|---|---|
| Ingredient | 12.5/500 [mg] | 12.5/850 [mg] | 12.5/1000 [mg] |
| Iron oxide, black | 0.15 | 0.20 | 0.225 |
| Iron oxide, red | 0.03 | 0.04 | 0.045 |
| Drug-layer (drug-loading): | (32.5) | (32.5) | (32.5) |
| Compound (I.9), or crystalline form (I.9X) of compound (I.9)) | 12.50 | 12.50 | 12.50 |
| Hypromellose 2910 | 18.00 | 18.00 | 18.00 |
| Propylene glycol | 2.00 | 2.00 | 2.00 |
| Over-coat (over-coating): | (12) | (16) | (18) |
| Hypromellose 2910 | 6.00 | 8.00 | 9.00 |
| Propylene glycol | 0.60 | 0.80 | 0.90 |
| Talc | 2.22 | 2.96 | 3.33 |
| Titanium dioxide | 3.00 | 4.00 | 4.50 |
| Iron oxide, black | 0.15 | 0.20 | 0.225 |
| Iron oxide, red | 0.03 | 0.04 | 0.045 |
| Total Mass (film-coat) | 44.5 | 48.5 | 50.5 |
| Total Mass (coated tablet) | 614.5 | 1017.5 | 1190.5 |

A broad dose range of SGLT-2 inhibitor, eg. 1.25, 5 or 12.5 mg, could be used, in which case the amount of binder corn starch or microcrystalline cellulose is adjusted. Instead of corn starch, microcrystalline cellulose could be used. In the further description of the manufacturing procedure only corn starch is described.

Manufacturing Procedure (SGLT-2 Inhibitor-Drug Layering by Film-Coating on Metformin HCl Tablet):

SGLT-2 inhibitor (e.g. Compound (I.9), or crystalline form (I.9X) of compound (I.9))+metformin HCl FDC with drug coating is produced by a fluid-bed granulation process, a conventional tableting process, and film-coating process with three steps: seal-coating, drug-loading and over-coating. The over-coating may be able to be skipped by combining with the drug-loading, if the stability is acceptable.

Metformin HCl Tablets: Metformin HCl and corn starch, fluid-bed granulation is conducted by spraying of "Granulation Liquid" composed of copolyvidon (Kollidon VA64) and purified water. Alternatively, the SGLT-2 inhibitor is added as powder together with metformin-HCl and corn starch to the fluid bed granulator. After finishing of fluid-bed granulation, the granulate is sieved with a suitable screen. The sieved granulate is blended with colloidal anhydrous silica (Aerosil 200) and magnesium stearate as a lubricant. The final blend is compressed into the tablets with a conventional rotary press.

Narrative more specific description of the manufacturing process for the Metformin HCl-granulate:
a) Metformin HCl is sieved using a screen with a mesh size of 0.5 to 1 mm before weighing.
b) Copolyvidon is dissolved in purified water at ambient temperature with a propeller mixer to produce the "Granulation Liquid"
d) The "Granulation Liquid" is sprayed into the mixture for fluid-bed granulating under dry condition to avoid blocking during granulation.
e) At the end of spraying, the resultant granulate is dried at 70-80° C. until the desired LOD value (i.e. 0.8-2%, for example 1-2%), in case the LOD is more than 2%.
f) The granulate is sieved using a screen with a mesh size of 0.5 to 1.0 mm.
g) The sieved granulate and colloidal anhydrous silica (Aerosil 200) are blended with a suitable blender. Aerosil 200 should be sieved with a 0.5 mm-screen before use.
h) Magnesium stearate passed through a 0.5 mm sieve and added into the granulate. Subsequently "Final Blend" is produced by final blending in the blender.
i) The "Final Blend" is compressed into the tablets with a conventional rotary press.

Film-coating: The tablets are film-coated by (1) seal-coating: by an aqueous film-coating suspension, containing hypromellose as film-forming agent, polyethylene glycol (Macrogol, especially Macrogol 400, 6000 or 8000) as plasticizer, propylene glycol as alternative plasticizer, talc as glidant and the pigments yellow iron oxide and/or red iron oxide or mixtures with iron oxide black and titanium dioxide, (2) drug-loading: by an aqueous film-coating suspension, containing hypromellose as film-forming agent, polyethylene glycol or propylene glycol as plasticizer, compound (I.9), or crystalline form (I.9X) of compound (I.9) as drug substance and (3) over-coating: by an aqueous film-coating suspension, containing hypromellose as film-forming agent, polyethylene glycol or propylene glycol as plasticizer, talc as glidant and the pigments yellow iron oxide and/or red and/or black iron oxide and titanium dioxide, Narrative more specific description of the manufacturing process for the film-coating with a coating machine:
a) Hypromellose and polyethylene glycol or propylene glycol are dissolved in purified water with a propeller mixer. Talc, titanium dioxide, and iron oxide (yellow, red, black or yellow and red and black and mixture thereof) are dispersed in purified water with a homo-mixer. The suspension is added into the hypromellose solution, then mixed with a propeller mixer at ambient temperature to produce the "Coating Suspension" for "seal-coating" and "over-coating".
b) Hypromellose, polyethylene glycol or propylene glycol are dissolved in purified water with a propeller mixer. Compound (I.9), or crystalline form (I.9X) of compound (I.9) (active drug) is added into the hypromellose solution, then dispersed with a propeller mixer at ambient temperature to produce the "Drug Suspension" for "drug-loading".
c) The Metformin HCl tablets are coated with the "Coating Suspension" to the target weight gain to form the "seal-coat". The "Coating Suspension" should be stirred again before use and kept stirring slowly during the coating (spraying) process.
d) Following the seal-coating, the "Drug Suspension" is applied to the surface of the Metformin HCl tablets to form the "drug layer" (drug loading). The "Drug Suspension" should be stirred again before use and kept stirring slowly during the coating (spraying) process. The coating end point can be determined by available PAT (Process Analysis Technology).
e) After drug loading the "Coating Suspension" is applied to the compound (I.9), or crystalline form (I.9X) of compound (I.9) drug-loaded tablets to form the "over-coat" and to produce the "Film-coated Tablets". The "Coating Suspension" should be stirred again before use and kept stirring slowly during the coating (spraying) process.

Product Description:

The product description of Compound (I.9), or crystalline form (I.9X) of compound (I.9)+Metformin HCl FDC monolayer tablets (tablet core and film-coated tablets) is shown in Table 8 and Table 9, respectively.

TABLE 8

Product Description of Compound (I.9), or crystalline form (I.9X) of compound (I.9) + Metformin HCl FDC Mono-layer Tablets (Tablet Core)

| Items | Dose Strength (SGLT-2 inhibitor/metformin HCl), mg | | |
|---|---|---|---|
| | 5 or 12.5/500 | 5 or 12.5/850 | 5 or 12.5/1000 |
| Tablet shape | Oval, biconvex | Oval, biconvex | Oval, biconvex |
| Core tablet size [mm] | 16.2 × 8.5 | 19.1 × 9.3 | 21.0 × 9.6 |
| Color | | white | |
| Weight | 590 | 1000 | 1180 |
| Crushing strength [N], (Mean) | ≥100 | ≥150 | ≥150 |
| Disintegration time [min] | ≤15 | ≤15 | ≤15 |
| Friability [%] | ≤0.5 | ≤0.5 | ≤0.5 |

| Items | Dose Strength (SGLT-2 inhibitor/metformin HCl), mg | | |
|---|---|---|---|
| | 5 or 12.5/500 | 5 or 12.5/850 | 5 or 12.5/1000 |
| Tablet shape | Oval, biconvex | Oval, biconvex | Oval, biconvex |
| Core tablet size [mm] | 16.2 × 8.5 | 19.1 × 9.3 | 21.0 × 9.6 |
| Color | | white | |
| Weight | 590 | 1003 | 1180 |
| Crushing strength [N], (Mean) | ≥100 | ≥150 | ≥150 |
| Disintegration time [min] | ≤15 | ≤15 | ≤15 |
| Friability [%] | ≤0.5 | ≤0.5 | ≤0.5 |

TABLE 9

Product Description of Compound (I.9), or crystalline form (I.9X) of compound (I.9) + Metformin HCl FDC Mono-layer Tablets (Coated)

| Items | Dose Strength (SGLT-2/metformin HCl), mg | | |
|---|---|---|---|
| | 5 or 12.5/500 | 5 or 12.5/850 | 5 or 12.5/1000 |
| Color | yellow/red/black mixtures or red/black mixtures | yellow/red/black mixtures or red/black mixtures | yellow/red/black mixtures or red/black mixtures |
| Weight | 602 | 1016 | 1198 |
| Crushing strength [N] (Mean) | ≥120 | ≥160 | ≥160 |
| Disintegration time [min] | ≤15 | ≤15 | ≤15 |

| Items | Dose Strength (SGLT-2/metformin HCl), mg | | |
|---|---|---|---|
| | 5 or 12.5/500 | 5 or 12.5/850 | 5 or 12.5/1000 |
| Color | red/black mixtures | red/black mixtures | red/black mixtures |
| Weight | 602 | 1020 | 1199 |
| Crushing strength [N] (Mean) | ≥120 | ≥160 | ≥160 |
| Disintegration time [min] | ≤15 | ≤15 | ≤15 |

Stability Data:

Stability data of Compound (I.9), or crystalline form (I.9X) of compound (I.9)+Metformin HCl FDC mono-layer tablets (Table 1.1 and 1.7) is shown in the following tables.

| 12.5 + 500 mg tablets | | |
|---|---|---|
| | Test parameter | |
| | 60° C. glass bottle | |
| | Initial | 8 W |
| Degradation compound (I.9), or crystalline form (I.9X) of compound (I.9) (%) | | <0.2 |
| Degradation Metformin (%) | <0.2 | <0.2 |
| Total | | <0.2 |

| 12.5 + 500 mg tablets | | |
|---|---|---|
| | Test parameter | |
| | 40° C. glass bottle | |
| | Initial | 8 W |
| Degradation compound (I.9), or crystalline form (I.9X) of compound (I.9) (%) | | <0.2 |
| Degradation Metformin (%) | <0.2 | <0.2 |
| Total | <0.2 | <0.2 |

| 12.5 + 500 mg tablets | | |
|---|---|---|
| | Test parameter | |
| | 40° C. glass bottle, open | |
| | Initial | 8 W |
| Degradation compound (I.9), or crystalline form (I.9X) of compound (I.9)) (%) | | <0.2 |
| Degradation Metformin (%) | <0.2 | <0.2 |
| Total | <0.2 | <0.2 |

| 12.5 + 500 mg tablets | | |
|---|---|---|
| | Test parameter | |
| | 60° C. glass bottle, with NaCL | |
| | Initial | 8 W |
| Degradation compound (I.9), or crystalline form (I.9X) of compound (I.9)) (%) | | 1.0 |
| Degradation Metformin (%) | <0.2 | <0.2 |
| Total | <0.2 | 1.0 |

| 1.25 + 500 mg tablets | | |
|---|---|---|
| | Test parameter | |
| | 60° C. glass bottle | |
| | Initial | 8 W |
| Degradation compound (I.9), or crystalline form (I.9X) of compound (I.9) (%) | | <0.2 |
| Degradation Metformin (%) | <0.2 | <0.2 |
| Total | | <0.2 |

| 1.25 + 500 mg tablets | | |
| --- | --- | --- |
| | Test parameter | |
| | | 40° C. glass bottle |
| | Initial | 8 W |
| Degradation compound (I.9), or crystalline form (I.9X) of compound (I.9) (%) | | <0.2 |
| Degradation Metformin (%) | <0.2 | <0.2 |
| Total | <0.2 | <0.2 |

| 1.25 + 500 mg tablets | | |
| --- | --- | --- |
| | Test parameter | |
| | | 40° C. glass bottle, open |
| | Initial | 8 W |
| Degradation compound (I.9), or crystalline form (I.9X) of compound (I.9)) (%) | | <0.2 |
| Degradation Metformin (%) | <0.2 | <0.2 |
| Total | <0.2 | <0.2 |

| 1.25 + 500 mg tablets | | |
| --- | --- | --- |
| | Test parameter | |
| | | 60° C. glass bottle, with NaCL |
| | Initial | 8 W |
| Degradation compound (I.9), or crystalline form (I.9X) of compound (I.9)) (%) | | 1.0 |
| Degradation Metformin (%) | <0.2 | <0.2 |
| Total | <0.2 | 1.0 |

Stability Data:

Stability data of Compound (I.9), or crystalline form (I.9X) of compound (I.9)+Metformin HCl FDC mono-layer tablets (Table 1.9 and 1.10) is shown in the following tables.

| 12.5 + 500 mg tablets | | |
| --- | --- | --- |
| | Test parameter | |
| | | 60° C. glass bottle |
| | Initial | 8 W |
| Degradation compound (I.9), or crystalline form (I.9X) of compound (I.9) (%) | | <0.2 |
| Degradation Metformin (%) | <0.2 | <0.2 |
| Total | | <0.2 |

| 12.5 + 500 mg tablets | | |
| --- | --- | --- |
| | Test parameter | |
| | | 40° C. glass bottle |
| | Initial | 8 W |
| Degradation compound (I.9), or crystalline form (I.9X) of compound (I.9) (%) | | <0.2 |
| Degradation Metformin (%) | <0.2 | <0.2 |
| Total | <0.2 | <0.2 |

| 12.5 + 500 mg tablets | | |
| --- | --- | --- |
| | Test parameter | |
| | | 40° C. glass bottle, open |
| | Initial | 8 W |
| Degradation compound (I.9), or crystalline form (I.9X) of compound (I.9)) (%) | | <0.2 |
| Degradation Metformin (%) | <0.2 | <0.2 |
| Total | <0.2 | <0.2 |

| 12.5 + 500 mg tablets | | |
| --- | --- | --- |
| | Test parameter | |
| | | 60° C. glass bottle, with NaCL |
| | Initial | 8 W |
| Degradation compound (I.9), or crystalline form (I.9X) of compound (I.9) (%) | | 1.3 |
| Degradation Metformin (%) | <0.2 | <0.2 |
| Total | <0.2 | 1.3 |

| 1.25 + 500 mg tablets | | |
| --- | --- | --- |
| | Test parameter | |
| | | 60° C. glass bottle |
| | Initial | 8 W |
| Degradation compound (I.9), or crystalline form (I.9X) of compound (I.9) (%) | | <0.2 |
| Degradation Metformin (%) | <0.2 | <0.2 |
| Total | | <0.2 |

| 1.25 + 500 mg tablets | | |
| --- | --- | --- |
| | Test parameter | |
| | | 40° C. glass bottle |
| | Initial | 8 W |
| Degradation compound (I.9), or crystalline form (I.9X) of compound (I.9) (%) | | <0.2 |
| Degradation Metformin (%) | <0.2 | <0.2 |
| Total | <0.2 | <0.2 |

| 1.25 + 500 mg tablets | | |
|---|---|---|
| | Test parameter | |
| | Initial | 40° C. glass bottle, open 8 W |
| Degradation compound (I.9), or crystalline form (I.9X) of compound (I.9)) (%) | | <0.2 |
| Degradation Metformin (%) | <0.2 | <0.2 |
| Total | <0.2 | <0.2 |

| 1.25 + 500 mg tablets | | |
|---|---|---|
| | Test parameter | |
| | Initial | 60° C. glass bottle, with NaCL 8 W |
| Degradation compound (I.9), or crystalline form (I.9X) of compound (I.9)) (%) | | 1.6 |
| Degradation Metformin (%) | <0.2 | <0.2 |
| Total | <0.2 | 1.6 |

The invention claimed is:

1. A pharmaceutical composition comprising a SGLT-2 inhibitor, a partner drug, and one or more pharmaceutical excipients, wherein the SGLT-2 inhibitor is 1-chloro-4-(β-D-glucopyranos-1-yl)-2-[4-((S)-tetrahydrofuran-3-yloxy)-benzyl]-benzene and wherein the partner drug is metformin hydrochloride, wherein the SGLT-2 inhibitor and metformin hydrochloride are present in a dosage strength of 5 mg/500 mg, 5 mg/850 mg, 5 mg/1,000 mg, 12.5 mg/500 mg, 12.5 mg/850 mg or 12.5 mg/1,000 mg, and wherein said one or more pharmaceutical excipients comprise of one or more fillers comprising microcrystalline cellulose (MCC), D-mannitol, corn starch or pregelatinized starch and a binder comprising copovidone, wherein said pharmaceutical composition is in the dosage form of a tablet, wherein said pharmaceutical composition is an immediate release dosage form, and wherein in a dissolution test after 45 minutes at least 75% by weight of each of the SGLT-2 inhibitor and partner drug is dissolved,
  wherein the tablet is a mono-layer tablet,
  wherein the tablet comprises a film-coat,
  wherein said tablet comprises 3.9-8.3% of said binder by weight of total coated tablet mass.

2. The pharmaceutical composition according to claim 1, wherein the excipients are selected from the group consisting of one or more fillers comprising microcrystalline cellulose (MCC), D-mannitol, corn starch and pregelatinized starch; a binder comprising copovidone; a lubricant comprising magnesium stearate or sodium stearyl fumarate; and a glidant comprising colloidal anhydrous silica.

3. The pharmaceutical composition according to claim 1, further comprising one or more of the following: the filler corn starch, the lubricant magnesium stearate or sodium stearyl fumarate and the glidant colloidal anhydrous silica.

4. The pharmaceutical composition according to claim 1, further comprising one or more of the following: the filler microcrystalline cellulose, the lubricant magnesium stearate or sodium stearyl fumarate and the glidant colloidal anhydrous silica.

5. The pharmaceutical composition according to claim 1, further comprising one or more of the following: the filler microcrystalline cellulose, the lubricant sodium stearyl fumarate and the glidant colloidal anhydrous silica.

6. The pharmaceutical composition according to claim 1, wherein the film-coat comprises a film-coating agent comprising hypromellose; a plasticizer comprising propylene glycol or polyethylene glycol; optionally a glidant comprising talc, and optionally one or more pigments comprising titanium dioxide, iron oxide red and/or iron oxide yellow and/or iron oxide black and mixture thereof.

7. The pharmaceutical composition according to claim 1, wherein the SGLT-2 inhibitor and metformin hydrochloride are present in a dosage strength of 5 mg/500 mg.

8. The pharmaceutical composition according to claim 1, wherein the SGLT-2 inhibitor and metformin hydrochloride are present in a dosage strength of 5 mg/1,000 mg.

9. The pharmaceutical composition according to claim 1, wherein the SGLT-2 inhibitor and metformin hydrochloride are present in a dosage strength of 12.5 mg/500 mg.

10. The pharmaceutical composition according to claim 1, wherein the SGLT-2 inhibitor and metformin hydrochloride are present in a dosage strength of 12.5 mg/1,000 mg.

11. The pharmaceutical composition according to claim 1, further comprising a lubricant.

12. The pharmaceutical composition according to claim 11, wherein said lubricant comprises magnesium stearate or sodium stearyl fumarate.

13. The pharmaceutical composition according to claim 11, wherein said tablet comprises 0.7-1.5% of said lubricant by weight of total coated tablet mass.

14. The pharmaceutical composition according to claim 1, further comprising a glidant.

15. The pharmaceutical composition according to claim 14, wherein said glidant comprises colloidal anhydrous silica.

16. The pharmaceutical composition according to claim 14, wherein said tablet comprises 0.05-0.5% of said glidant by weight of total coated tablet mass.

17. The pharmaceutical composition according to claim 1, further comprising a lubricant and a glidant.

18. The pharmaceutical composition according to claim 17, wherein said lubricant comprises magnesium stearate or sodium stearyl fumarate and said glidant comprises colloidal anhydrous silica.

19. The pharmaceutical composition according to claim 17, wherein said tablet comprises 0.7-1.5% of said lubricant and 0.05-0.5% of said glidant by weight of total coated tablet mass.

20. The pharmaceutical composition according to claim 1, wherein said tablet comprises 2.3-8.0% corn starch, 0-4.4% pregelatinized starch and 0-33% D-mannitol by weight of total coated tablet mass.

21. The pharmaceutical composition according to claim 1, wherein said tablet comprises 0.1-2.11% of said SGLT-2 inhibitor and 47-88% metformin hydrochloride by weight of total coated tablet mass.

22. The pharmaceutical composition according to claim 1, further comprising a disintegrant.

23. The pharmaceutical composition according to claim 22, wherein said disintegrant comprises crospovidone or croscarmellose sodium.

24. The pharmaceutical composition according to claim 1, comprising (% by weight of total coated tablet mass):
  0.1-2.11% SGLT-2 inhibitor,
  47-88% metformin hydrochloride,
  2.3-8.0% corn starch, 0-4.4% pregelatinized starch,
0-33% D-mannitol, and
0.7-1.5% magnesium stearate,
said pharmaceutical composition further comprising (% by weight of total coated tablet mass):
0.05-0.5% colloidal anhydrous silica, and
0.00-3.0% disintegrant.

25. The pharmaceutical composition according to claim 24, wherein said disintegrant is crospovidone or croscarmellose sodium.

26. The pharmaceutical composition according to claim 7, comprising 30.130 mg corn starch, and 47.200 mg copovidone, said pharmaceutical composition further comprising 2.950 mg colloidal anhydrous silica and 4.720 mg magnesium stearate.

27. The pharmaceutical composition according to claim 8, comprising 65.260 mg corn starch, and 94.400 mg copovidone, said pharmaceutical composition further comprising 5.900 mg colloidal anhydrous silica and 9.440 mg magnesium stearate.

28. The pharmaceutical composition according to claim 9, comprising 22.630 mg corn starch, and 47.200 mg copovidone, said pharmaceutical composition further comprising 2.950 mg colloidal anhydrous silica and 4.720 mg magnesium stearate.

29. The pharmaceutical composition according to claim 10, comprising 57.760 mg corn starch, and 94.400 mg copovidone, said pharmaceutical composition further comprising 5.900 mg colloidal anhydrous silica and 9.440 mg magnesium stearate.

* * * * *